(12) United States Patent
Gribetz

(10) Patent No.: US 11,467,665 B2
(45) Date of Patent: Oct. 11, 2022

(54) VIRTUAL USER INTERFACE SYSTEM AND METHODS FOR USE THEREOF

(71) Applicant: Meron Gribetz, New York City, NY (US)

(72) Inventor: Meron Gribetz, New York City, NY (US)

(73) Assignee: Meron Gribetz, New York City, NY (US)

( * ) Notice: Subject to any disclaimer, the term of this patent is extended or adjusted under 35 U.S.C. 154(b) by 29 days.

(21) Appl. No.: 17/251,829

(22) PCT Filed: Jun. 13, 2019

(86) PCT No.: PCT/IB2019/054948
§ 371 (c)(1),
(2) Date: Dec. 14, 2020

(87) PCT Pub. No.: WO2019/239367
PCT Pub. Date: Dec. 19, 2019

(65) Prior Publication Data
US 2021/0255707 A1    Aug. 19, 2021

Related U.S. Application Data

(60) Provisional application No. 62/684,756, filed on Jun. 14, 2018.

(51) Int. Cl.
*G06F 3/01* (2006.01)
*A61F 2/70* (2006.01)

(52) U.S. Cl.
CPC ............... *G06F 3/015* (2013.01); *A61F 2/70* (2013.01)

(58) Field of Classification Search
CPC ...................................................... G06F 3/015
(Continued)

(56) References Cited

U.S. PATENT DOCUMENTS

| 4,328,813 A | 5/1982 | Ray |
| 4,551,149 A | 11/1985 | Sciarra |

(Continued)

FOREIGN PATENT DOCUMENTS

| EP | 2835988 | 2/2015 |
| EP | 2038004 | 1/2018 |

(Continued)

OTHER PUBLICATIONS

International Preliminary Report on Patentability dated Apr. 30, 2021 From the International Preliminary Examining Authority Re. Application No. PCT/IB2020/050527. (45 Pages).

(Continued)

*Primary Examiner* — Calvin C Ma

(57) ABSTRACT

A system including a power source, one or more stimulating devices for stimulating the visual cortex of a user to present a perceived virtual image responsive to the stimulating, one or more sensing devices for sensing electrical signals in the motor and/or pre-motor cortex of the user and a processor/controller connected to the stimulating and sensing devices and programmed to sense signals from the motor and/or pre-motor cortex of the user. The sensed signals result from the user performing a movement and/or intending to perform a movement and/or imagining the performing of a movement and are used to interact with the presented virtual image. The processor/controller processes the sensed signals to obtain computed data indicative of a user's interaction with the virtual image, and performs a general computing task responsive to the computed data.

33 Claims, 7 Drawing Sheets

(58) Field of Classification Search
USPC .......................................................... 345/158
See application file for complete search history.

(56) References Cited

U.S. PATENT DOCUMENTS

| | | | |
|---|---|---|---|
| 5,895,416 | A | 4/1999 | Barreras, Sr. et al. |
| 6,178,353 | B1 | 1/2001 | Griffith et al. |
| 6,246,911 | B1 | 6/2001 | Seligman |
| 6,463,328 | B1 | 10/2002 | John |
| 6,782,292 | B2 | 8/2004 | Whitehurst |
| 6,909,917 | B2 | 6/2005 | Woods et al. |
| 7,120,486 | B2 | 10/2006 | Leuthardt et al. |
| 7,177,678 | B1 | 2/2007 | Osario et al. |
| 7,346,391 | B1 | 3/2008 | Osorio et al. |
| 7,353,065 | B2 | 4/2008 | Morrell |
| 7,532,935 | B2 | 5/2009 | Maschino et al. |
| 7,890,182 | B2 | 2/2011 | Parramon et al. |
| 8,065,012 | B2 | 11/2011 | Firlik et al. |
| 8,121,694 | B2 | 2/2012 | Molnar et al. |
| 8,262,714 | B2 | 9/2012 | Hulvershorn et al. |
| 8,380,314 | B2 | 2/2013 | Panken et al. |
| 8,396,557 | B2 | 3/2013 | DiLorenzo |
| 8,412,334 | B2 | 4/2013 | Whitehurst et al. |
| 8,868,173 | B2 | 10/2014 | Nelson et al. |
| 8,914,115 | B2 | 12/2014 | Giftakis et al. |
| 8,914,119 | B2 | 12/2014 | Wu et al. |
| 8,936,630 | B2 | 1/2015 | Denison et al. |
| 9,079,039 | B2 | 7/2015 | Carlson et al. |
| 9,084,901 | B2 | 7/2015 | Wahlstrand |
| 9,173,811 | B2 | 11/2015 | Greiner et al. |
| 9,198,828 | B2 | 12/2015 | Greiner et al. |
| 9,327,069 | B2 | 5/2016 | Foster et al. |
| 9,352,145 | B2 | 5/2016 | Whitehurst et al. |
| 9,381,346 | B2 | 7/2016 | Lee et al. |
| 9,409,030 | B2 | 8/2016 | Perryman et al. |
| 9,511,223 | B2 | 12/2016 | DeGiorgio et al. |
| 9,566,449 | B2 | 2/2017 | Perryman et al. |
| 9,597,494 | B2 | 3/2017 | Wingeier et al. |
| 9,782,593 | B2 | 10/2017 | Parramon et al. |
| 9,925,384 | B2 | 3/2018 | Perryman et al. |
| 9,949,376 | B2 | 4/2018 | Greenberg et al. |
| 10,025,375 | B2* | 7/2018 | Lazor ...................... G06T 19/20 |
| 10,149,958 | B1* | 12/2018 | Tran ........................ G06V 40/19 |
| 10,201,708 | B2 | 2/2019 | De Ridder |
| 10,220,211 | B2 | 3/2019 | Liao |
| 10,471,262 | B2 | 11/2019 | Perryman et al. |
| 2002/0087201 | A1 | 7/2002 | Firlik et al. |
| 2006/0122660 | A1 | 6/2006 | Boveja et al. |
| 2007/0043401 | A1 | 2/2007 | John |
| 2007/0179558 | A1 | 8/2007 | Gliner et al. |
| 2008/0161880 | A1 | 7/2008 | Firlik et al. |
| 2009/0112278 | A1 | 4/2009 | Wingeier et al. |
| 2009/0118804 | A1 | 5/2009 | Moffitt et al. |
| 2011/0009922 | A1 | 1/2011 | Assaf et al. |
| 2011/0137381 | A1 | 6/2011 | Lee et al. |
| 2011/0264165 | A1 | 10/2011 | Molnar et al. |
| 2011/0295338 | A1 | 12/2011 | Rickert et al. |
| 2012/0108998 | A1 | 5/2012 | Molnar et al. |
| 2012/0296444 | A1 | 11/2012 | Greenberg et al. |
| 2014/0058528 | A1 | 2/2014 | Contreras-Vidal et al. |
| 2014/0142669 | A1 | 5/2014 | Cook et al. |
| 2014/0200432 | A1 | 7/2014 | Banerji et al. |
| 2014/0214125 | A1 | 7/2014 | Greiner et al. |
| 2014/0237073 | A1 | 8/2014 | Schiff |
| 2014/0277019 | A1 | 8/2014 | Pearson |
| 2015/0105837 | A1 | 4/2015 | Aguilar Domingo |
| 2015/0119689 | A1 | 4/2015 | Pascual-Leone et al. |
| 2016/0206883 | A1 | 7/2016 | Bornzin et al. |
| 2016/0354095 | A1 | 12/2016 | Pearson |
| 2017/0042474 | A1 | 2/2017 | Widge et al. |
| 2017/0043167 | A1 | 2/2017 | Widge et al. |
| 2017/0202475 | A1 | 7/2017 | Leuthardt |
| 2017/0259064 | A1 | 9/2017 | Wu et al. |
| 2018/0036537 | A1 | 2/2018 | Van den Heuvel |
| 2018/0153474 | A1 | 6/2018 | Aeschlimann et al. |
| 2018/0289311 | A1 | 10/2018 | Phillips |
| 2018/0353759 | A1 | 12/2018 | Starr et al. |
| 2019/0090749 | A1 | 3/2019 | Leuthardt et al. |
| 2019/0216342 | A1 | 7/2019 | Williams et al. |
| 2019/0217112 | A1 | 7/2019 | Williams et al. |
| 2019/0217113 | A1 | 7/2019 | Williams et al. |
| 2019/0217116 | A1 | 7/2019 | Williams et al. |
| 2019/0346925 | A1* | 11/2019 | Daniels ................... G06F 3/013 |
| 2020/0023189 | A1 | 1/2020 | Gribetz et al. |
| 2020/0330749 | A1 | 10/2020 | Gribetz et al. |
| 2021/0361948 | A1 | 11/2021 | Leuthardt et al. |
| 2022/0117540 | A1 | 4/2022 | Leuthardt et al. |

FOREIGN PATENT DOCUMENTS

| | | |
|---|---|---|
| JP | 2013-527784 | 7/2013 |
| JP | 2014-079387 | 5/2014 |
| JP | 2016-517283 | 6/2018 |
| WO | WO 2005/039696 | 5/2005 |
| WO | WO 2006/029007 | 3/2006 |
| WO | WO 2007/138598 | 12/2007 |
| WO | WO 2009/044271 | 4/2009 |
| WO | WO 2009/067323 | 5/2009 |
| WO | WO 2010/056751 | 5/2010 |
| WO | WO 2011/123150 | 10/2011 |
| WO | WO 2014/078074 | 5/2014 |
| WO | WO 2014/130960 | 8/2014 |
| WO | WO 2015/164477 | 10/2015 |
| WO | WO 2015/195553 | 12/2015 |
| WO | WO 2016/049789 | 4/2016 |
| WO | WO 2016/118811 | 7/2016 |
| WO | WO 2017/199052 | 11/2017 |
| WO | WO 2018/109715 | 6/2018 |
| WO | WO 2019/130248 | 7/2019 |
| WO | WO2019/239367 | 12/2019 |
| WO | WO 2019/244099 | 12/2019 |
| WO | WO 2020/161555 | 8/2020 |
| WO | WO 2021/144730 | 7/2021 |

OTHER PUBLICATIONS

Examination Report Under Sections 12 & 13 of the Patents Act, 1970 and the Patents Rules, 2003 dated Aug. 12, 2021 From the Government of India, Intellectual Property India, Patents, Designs, Trade Marks, Geographical Indications, The Patent Office Re. Application No. 201927028238. (6 Pages).

Paniccia et al. "Clinical and Non-Clinical Depression and Anxiety in Young People: A Scoping Review on Heart Rate Variability", Autonomic Neuroscience: Basic and Clinical, 208: 1-14, Published Online Aug. 26, 2017.

Sgoifo et al. "Autonomic Dysfunction and Heart Rate Variability in Depression", Stress, 18(3): 343-352, Published Online May 25, 2015.

Siddiqi et al. "Repetetive Transcranial Magnetic Stimulation With Resting-State Network Targeting for Treatment-Resistant Depression in Traumatic Brain Injury: A Randomized, Controlled, Double-Blinded Pilot Study", Journal of Neurotrauma, 36(8): 1361-1374, Published Online Jan. 7, 2019.

International Preliminary Report on Patentability dated Jul. 9, 2020 From the International Bureau of WIPO Re. Application No. PCT/IB2018/060667. (8 Pages).

International Preliminary Report on Patentability dated Dec. 24, 2020 From the International Bureau of WIPO Re. Application No. PCT/IB2019/054948. (8 Pages).

International Preliminary Report on Patentability dated Jun. 27, 2019 From the International Bureau of WIPO Re. Application No. PCT/IB2017/057952. (9 Pages).

International Preliminary Report on Patentability dated Dec. 30, 2020 From the International Bureau of WIPO Re. Application No. PCT/IB2019/055217. (9 Pages).

International Search Report and the Written Opinion dated Apr. 10, 2019 From the International Searching Authority Re. Application No. PCT/IB2018/060667. (14 Pages).

(56) References Cited

OTHER PUBLICATIONS

International Search Report and the Written Opinion dated Dec. 13, 2019 From the International Searching Authority Re. Application No. PCT/IB2019/055217. (15 Pages).
International Search Report and the Written Opinion dated Apr. 16, 2020 From the International Searching Authority Re. Application No. PCT/IB2020/050527. (16 Pages).
International Search Report and the Written Opinion dated Oct. 16, 2019 From the International Searching Authority Re. Application No. PCT/IB2019/054948. (13 Pages).
International Search Report and the Written Opinion dated Mar. 22, 2018 From the International Searching Authority Re. Application No. PCT/IB2017/057952. (16 Pages).
Invitation to Pay Additional Fees dated Oct. 15, 2019 From the International Searching Authority Re. Application No. PCT/IB2019/055217. (2 Pages).
Written Opinion dated Dec. 21, 2020 From the International Preliminary Examining Authority Re. Application No. PCT/IB2020/050527. (9 Pages).
Albert et al. "Deep Brain Stimulation, Vagal Nerve Stimulation and Transcranial Stimulation: An Overview of stimulation Parameters and Neurotransmitter Release", Neuroscience & Biobehavioral Reviews,33(7):1042-1060, Jul. 2009.
Alesci et al. "Major Depression is Associated with Significant Diurnal Elevations in Plasma Interleukin-6 Levels, a Shift of its Circadian Rhythm, and Loss of Physiological Complexity in its Secretion: Clinical Implications", The Journal of Clinical Endocrinology & Metabolism, 90(5): 2522-2530, May 1, 2005.
Allain et al. "Enzymatic Determination of Total Serum Cholesterol", Clinical Chemistry,20(4): 470-475, Apr. 1974.
American Psychiatric Association "Diagnostic and Statistical Manual of Mental Disorders: DSM-IV™", The American Psychiatric Association, Fourth Ed., p. 1-886, May 1994.
Asselbergs et al. "Mobile Phone-Based Unobtrusive Ecological Momentary Assessment of Day-to-Day Mood: An Explorative Study", Journal of Medical Internet Research,18(3):1-15, 2016.
Avery et al. "A Controlled Study of Repetitive Transcranial Magnetic Stimulation in Medication-Resistant Major Depression", Biological Psychiatry,59(2):187-194, Jan. 15, 2006.
Ballenger et al. "Carbamazepine in Manic-Depressive Illness: A New Treatment", The American Journal of Psychiatry, 137(7): 782-790, Jul. 1980.
Barker et al. "Non-Invasive Magnetic Stimulation of Human Moto Cortex", The Lancet 325:1106-1107, 1985.
Behrend et al. "Toward Feedback Controlled Deep Brain Stimulation: Dynamics of Glutamate Release in the Subthalamic Nucleus in Rats",Journal of Neuroscience Methods,180(2): 278-289, Jun. 15, 2009.
Bejjani et al. "Transient Acute Depression Induced by High-Frequency Deep-Brain Stimulation", The New England Journal of Medicine, 340:1476-1480,May 13, 1999.
Belmaker et al. "Major Depressive Disorder", The New England Journal of Medicine, 358:55-68,Jan. 3, 2008.
Benabid et al. "Combined (Thalamotomy and Stimulation) Stereotactic Surgery of the VIM Thalamic Nucleus for Bilateral Parkinson Disease",Proceedings of the Meeting of the American Society for Stereotactic and Functional Neurosurgery, Applied Neurophysiology, 50: 344-346, 1987.
Ben-Menachem et al. "Effects of Vagus Nerve Stimulation on Amino Acids and Other Metabolites in the CSF of Patients with Partial Seizures", Epilepsy Research, 20(3):221-227, Mar. 1995.
Ben-Menachem et al. "Vagus Nerve Stimulation for Treatment of Partial Seizures: 1. A Controlled Study of Effect on Seizures", Epilepsia, 35(3):614-626, 1994.
Berndt et al. "Expanding the Optogenetics Toolkit: A Naturally Occurring Channel for Inhibitory Optogenetics is Discovered", Science, 349(6248): 590-591,Aug. 7, 2015.
Bhagwagar et al. "Persistent Reduction in Brain Serotonin1A Receptor Binding in Recovered Depressed Men Measured By Positron Emission Tomography with [11C]WAY-100635", Molecular Psychiatry, 9:386-392, Mar. 24, 2004.
Bichot et al. "A Source for Feature-Based Attention in the Prefrontal Cortex", Neuron 88(4): 832-844, Nov. 18, 2015.
Bick et al. "Neuromodulation for Restoring Memory", Neurosurgical Focus,40:1-12, May 2016.
Biederman et al. "A Fully-Integrated. Miniaturized (0.125 $mm^2$) 10.5 µW Wireless Neural Sensor", IEEE Journal of Solid-State Circuits. 48(4): 960-970, Apr. 2013.
Boyden et al. "Millisecond-Timescale, Genetically Targeted Optical Control of Neural Activity", Nature Neuroscience, 8(9): 1263-1268, Sep. 2005.
Bradley et al. "Influence of Child Abuse on Adult Depression Moderation by the Corticotropin-Releasing Hormone Receptor Gene",Arch Gen Psychiatry.65(2):190-200,Feb. 2008.
Brody et al. "Regional Brain Metabolic Changes in Patients With Major Depression Treated With Either Paroxetine or Interpersonal Therapy", Arch Gen Psychiatry.;58(7):631-640, Jul. 2001.
Bundy et al. "Decoding Three-Dimensional Reaching Movements Using Electrocorticographic Signals in Humans", Journal of Neural Engineering, 13(2):1-18, Feb. 23, 2016.
Burke et al. "Depression and Cortisol Responses toPpsychological Stress: A Meta-Analysis", Psychoneuroendocrinology 30(9): 846-856, Oct. 2005.
Butson et al. "Current Steering to Control the Volume of Tissue Activated During Deep Brain Stimulation", Brain Stimulation, 1(1): 7-15, Jan. 2008.
Carpenter et al. "Effect of Vagus Nerve Stimulation on Cerebrospinal Fluid Monoamine Metabolites, Norepinephrine, and Gamma-AminobutyricAacid Concentrations in Depressed Patients", Biological Psychiatry, 56(6): 418-426, Sep. 15, 2004.
Carroll et al. "Pathophysiology o fHypercortisolism in Depression", Acta Psychiatrica Scandinavica 115 (Suppl. 433): 90-103, Feb. 2007.
Caspi et al. "Influence of Life Stress on Depression: Moderation By a Polymorphism in the 5-HTT Gene", Science, 301(5631): 386-389, Jul. 18, 2003.
Cepoiu et al. "Recognition of Depression By Non-Psychiatric Physicians—A Systematic Literature Review and Meta-Analysis", Journal of General Internal Medicine,23(1):25-36, Jan. 2008.
Cohen et al. "Developing a More Focal Magnetic Stimulator. Part I: Some Basic Principles", Journal of Clinical Neurophysiology, 8(1): 102-111, Jan. 1, 1991.
Collinger et al. "High-Performance Neuroprosthetic Control by an Individual with Tetraplegia", The Lancet, 381(9866): 557-564, Feb. 16-22, 2013.
Coppen "The Biochemistry of Affective Disorders", The British Journa of Psychiatry,113(504):1237-1264, Nov. 1967.
Coyne et al. "Prevalence, Depressive Nature, and Comorbidity of Disorders in Primary Care", General Hospital Psychiatry, 16: 267-276, 1994.
Cronin et al. "Task-Specific Somatosensory Feedback Via Cortical Stimulation in Humans", IEEE Transactions on Haptics, 9(4):512-522, Jul. 18, 2016.
Dantzer et al. "From Inflammation to Sickness and Depression: When the Immune System Subjugates the Brain", Nature Reviews Neuroscience, 9:46-56, Jan. 1, 2008.
Davidson et al. "Depression: Perspectives from Affective Neuroscience", Annual Review of Psychology, 53:545-574, Feb. 2002.
Deisseroth "Optogenetics: 10 years of Microbial Opsins in Neuroscience", Nature Neuroscience, 18(9): 1213-1225, Sep. 2015.
Deisseroth et al. "Optogenetics", Nature Methods, 8(1):26-29, Jan. 2011.
Depression Guideline Panel "Depression in Primary Care: Detection, Diagnosis, and Treatment", Journal of American Association of Nurse Practionars, 6(5): 224-238, May 1994.
Dimitriu et al. "Neurostimulatory Therapeutics in Management of Treatment-Resistant Depression with Focus on Deep Brain Stimulation", Mount Sinai Journal of Medicine, 75(3):263-275, Jun. 2008.
Dobelle "Artificial Vision for the Blind by Connecting a Television Camera to the Visual Cortex", ASAIO Journal, 46(1):3-9, Jan.-Feb. 2000.

(56) References Cited

OTHER PUBLICATIONS

Dobelle et al. "Artificial Vision for the Blind by Electrical Stimulation of the Visual Cortex", Neurosurgery, 5(4):521-527, Oct. 1, 1979.
Dobelle et al. "Artificial Vision for the Blind: Electrical Stimulation of Visual Cortex Offers Hope for a Functional Prosthesis", Science, 1834123):440-444, Feb. 1, 1974.
Dobelle et al. "'Braille' Reading by a Blind Volunteer by Visual Cortex Stimulation", Nature, 259:111-112, Jan. 15, 1976.
Dobelle et al. "Phosphenes Produced By Electrical Stimulation of Human Occipital Cortex, and Their Application to the Development of a Prosthesis for the Blind", The Journal of Physiology, 243(2):553-576, Dec. 1, 1974.
Doud et al. "Continuous Three-Dimensional Control of a Virtual Helicopter Using a Motor Imagery Based Brain-Computer Interface", PLoS One,6(10):1-10, Oct. 26, 2011.
Dougherty et al. "A Randomized Sham-Controlled Trial of Deep Brain Stimulation of the Ventral Capsule/Ventral Striatum for Chronic Treatment-Resistant Depression", Biological Psychiatry, 78(4):240-248, Aug. 15, 2015.
Duman et al. "A Molecular and Cellular Theory of Depression", Arch Gen Psychiatry,54(7):597-606,1997.
Duman et al. "A Neurotrophic Model for Stress-Related Mood Disorders", Biological Psychiatry, 59(12):1116-1127, Jun. 15, 2006.
Duman et al. "Neuronal Plasticity and Survival in Mood Disorders", Biological Psychiatry, 48(8): 732-739,Oct. 15, 2000.
Dumm et al. "Virtual Electrodes by Current Steering in Retinal Protheses", Investigational Ophthalmology & Visual Science, 55(12): 8077-8085, Dec. 2014.
Ellis et al. "Is Platelet Imipramine Binding Reduced in Depression? A Meta-Analysis", Biological Psychiatry, 36(5):292-299, Sep. 1, 1994.
Emiliani et al. "All-Optical Interrogation of Neural Circuits", Journal of Neuroscience 35(41):13917-13926, Oct. 14, 2015.
Fava "Diagnosis and Definition of Treatment-Resistant Depression", Biological Psychiatry, 53(8):649-659, Apr. 15, 2003.
Feng et al. "Toward Closed-ILop Optimization of Deep Brain Stimulation for Parkinson's Disease: Concepts and Lessons from a Computational Model", Journal of Neural Engineering, 4(2): 14-21, Feb. 23, 2007.
Figiel et al. "The Use of Rapid-Rate Transcranial Magnetic Stimulation (rTMS) in Refractory Depressed Patients", Journal of Neuropsychiatry, 10(1):20-25, Apr. 2006.
Fitzgerald et al. "A Randomized, Controlled Trial of Sequential Bilateral Repetitive Transcranial Magnetic Stimulation for Treatment-Resistant Depression", The American Journal of Psychiatry, 163(1):88-94,Jan. 2006.
Fitzgerald et al. "The Application of Transcranial Magnetic Stimulation in Psychiatry and Neurosciences Research", Acta Psichiatrica Scandinavica, 105(5():324-340, May 2002.
Fontaine et al. "Effect of Subthalamic Nucleus Stimulation on Obsessive-Compulsive Disorder in a Patient with Parkinson Disease," Journal of Neurosurgery 100 (2004):1084-1086.
Foster et al. "Reverse Replay of Behavioural Sequences in Hippocampal Place Cells During the Awake State.", Nature,440: 680-683, Mar. 30, 2006.
Frank et al. "Hold Your Horses: Impulsivity, Deep Brain Stimulation, and Medication in Parkinsonism", Science,318(23):1309-1312, Nov. 2007.
Fu et al. "Stable Long-Term Chronic Brain Mapping at the Single-Neuron Level", Nature Methods,13: 875-882, Aug. 29, 2016.
Gale et al. "Electrical Stimulation-Evoked Dopamine Release in the Primate Striatum", Stereotact Functional Neurosurgery,91(6):355-363, Nov. 2013.
Gale et al. "Reward and Reinforcement Activity in the Nucleus Accumbens During Learning", Frontiers in Behavioral Bioscience, 8, Art.114: 1-10, Apr. 2014.
Garrett et al. "EVestG(TM): Responses in Depressed Patients," 30th Annual International IEEE EMBS Conference Vancouver, British Columbia, Canada, Aug. 20-24, 2008, pp. 1707-1710.

George et al. "A One-Year Comparison of Vagus Nerve Stimulation with Treatment as Usual for Treatment-Resistant Depression", Biological Psychiatry, 58(5):364-373,Sep. 1, 2005.
George et al. "Vagus Nerve Stimulation: A New Tool for Brain Research and Therapy", Biological Psychiatry, 47(4):287-295,Feb. 15, 2000.
Goldapple et al. "Modulation of Cortical-Limbic Pathways in Major Depression: Treatment-Specific Effects of Cognitive Behavior Therapy", Arch Gen Psychiatry,61(1):34-41, 2004.
Golier et al. "Low Serum Cholesterol Level and Attempted Suicide", The American Journal of Psychiatry, 152(3):419-423, Apr. 2006.
Goodman et al. "Deep Brain Stimulation in Psychiatry: Concentrating on the Road Ahead", Biological Psychiatry, 65(4):263-266,Feb. 15, 2009.
Greenberg et al. "Three-Year Outcomes in Deep Brain Stimulation for Highly Resistant Obsessive-Compulsive Disorder", Neuropsychopharmacology, 31:2384-2393, Jul. 19, 2006.
Grossman et al. "Noninvasive Deep Brain Stimulation via Temporally Interfering Electric Fields", Cell,169(6): 1029-1041, Jun. 1, 2017.
Hacker et al. "Frequency-Specific Electrophysiologic Correlates of Resting State fMRI Networks", NeuroImage, 149: 446-457, Apr. 1, 2017.
Hacker et al. "Resting State Network Estimation in Individual Subjects", NeuroImage, 82: 616-633, Available Online Jun. 2, 2013.
Haelbig et al. "Pallidal Stimulation in Dystonia: Effects on Cognition, Mood, and Quality of Life", Journal of Neurology, Neurosurgery and Psychiatry,76(12):1713-1716, 2005.
Hamilton et al. "Neural Signal Processing and Closed-Loop Control Algorithm Design for an Implanted Neural Recording and Stimulation System", 37th Annual International Conference of the IEEE Engineering in Medicine and Biology Society (EMBC), 7831-7836, Aug. 2015.
Han et al. "Microelectrode Technologies for Deep Brain Stimulation", Implantable Neural Proteses, I. Devices and Applications, p. 195-219, Jun. 10, 2009.
Hardesty et al. "Deep Brain Stimulation in Movement and Psychiatric Disorders", Biological Psychiatry, 61(7):831-835, Apr. 1, 2007.
Heils et al. "Allelic Variation of Human Serotonin Transporter Gene Expression", Journal of Neurochemistry, 66(6):2621-2624, Jun. 1996.
Henry et al. "Brain Blood Flow Alterations Induced by Therapeutic Vagus Nerve Stimulation in Partial Epilepsy: I. Acute Effects at High and Low Levels of Stimulation", Epilepsia, 39(9):983-990, Sep. 1998.
Hochberg et al. "Neuronal Ensemble Control of Prosthetic Devices by a Human with Tetraplegia", Nature, 442:164-171, Jul. 13, 2006.
Holsboer "The Corticosteroid Receptor Hypothesis of Depression", Neuropsychopharmacology, 23:477-501, Nov. 1, 2000.
Holsboer et al. "Antidepressants and Hypothalamic-Pituitary-Adrenocortical Regulation", Endocrine Reviews,17(2): 187-205, Apr. 1, 1996.
Hong et al. "Syringe Injectable Electronics: Precise Targeted Delivery with Quantitative Input/Output Connectivity", Nano Letters, 15 (10): 6979-6984, 2015.
Jacobs et al. "Adult Brain Neurogenesis and Psychiatry: A Novel Theory of Depression", Molecular Psychiatry,5:262-269, Jun. 15, 2000.
Janicak et al. "Transcranial Magnetic Stimulation in the Treatment of Major Depressive Disorder: A Comprehensive Summary of Safety Experience From Acute Exposure, Extended Exposure, and During Reintroduction Treatment", Journal of Clinical Psychiatry, 69(222-232), Feb. 2008.
Jarosiewicz et al. "Virtual Typing By People with Tetraplegia Using a Self-Calibrating Intracortical Braincomputer Interface", Science Translational Medicine 11;7(313): 28P. Nov. 2015.
Jiminez et al. "A Patient with a Resistant Major Depression Disorder Treated with Deep Brain Stimulation in the Inferior Thalamic Peduncle", Neurosurgery, 57(3):585-593, Sep. 1, 2005.
Judd et al. "A Prospective 12-Year Study of Subsyndromal and Syndromal Depressive Svmptoms in Unipolar Major Depressive Disorders", Arch Gen Psychiatry,55(8):694-700, Aug. 1998.

(56) References Cited

OTHER PUBLICATIONS

Karege et al. "Decreased Serum Brain-Derived Neurotrophic Factor Levels in Major Depressed Patients", Psychiatry Research, 109(2):143-148, Mar. 15, 2002.

Katnani et al. Temporally Coordinated Deep Brain Stimulation in the Dorsal and Ventral Striatum Synergistically Enhances Associative Learning, Scientific Reports, 6:1-8, Jan. 4, 2016.

Kearns et al. "A Comparison of Depression Rating Scales", The Britissh Journal of Psychiatry, 141(1): 45-49, Jul. 1982.

Kempermann et al. "Depressed New Neurons?—Adult Hippocampal Neurogenesis and a Cellular Plasticity Hypothesis of Major Depression", Biological Psychiatry, 54(5):499-503, Sep. 1, 2003.

Kendler et al. "The Interaction of Stressful Life Events and a Serotonin Transporter Polymorphism in the Prediction of Episodes of Major Depression", Arch Gen Psychiatry, 62(5):529-535, May 2005.

Kennedy et al. "Direct Control of a Computer from the Human Central Nervous System", IEEE Transactions on Rehabilitation Engineering, 8(2): 198-202, Jun. 2000.

Kessler et al. "Lifetime Prevalence and Age-of-Onset Distributions of DSM-IV Disorders in the National Comorbidity Survey Replication", Archives of General Psychiatry, 62(6): 593-602, Jun. 2005.

Kessler et al. "The Epidemiology of Major Depressive Disorder: Results From the National Comorbidity Survey Replication (NCS-R)", JAMA, 289(23):3095-3105, Jun. 18, 2003.

Kirsch et al. "Initial Severity and Antidepressant Benefits: A Meta-Analysis of Data Submitted to the Food and Drug Administration". PLOS Medicine, 5(2):260-268, Feb. 2008.

Kirsch et al. "The Emperor's New Drugs: An Analysis of Antidepressant Medication Data Submitted to the U.S. Food and Drug Administration", Prevention & Treatment,5, 1-11, Jul. 15, 2002.

Klein et al. Therapeutic Efficacy of Right Prefrontal Slow Repetitive Transcranial Magnetic Stimulation in Major Depression, A Double-Blind Controlled Study: Arch Gen Psychiatry. 56(4):315-320, 1999.

Klomp et al. "Fabrication of Large Arrays of Cortical Electrodes For Use in Man", Journal of Biomedical Materials Research Banner,11(3):347-364, May 1977.

Konsman et al. "Rat brain vascular distribution of interleukin-1 type-1 receptor immunoreactivity: relationship to patterns of inducible cyclooxygenase expression by peripheral inflammatory stimuli", The Journal of Comparitive Neurology, 472(1):113-129, Apr. 19, 2004.

Kosel et al. "Mood Improvement After Deep Brain Stimulation of the Internal Globus Pallidus for Tardive Dyskinesia in a Patient Suffering From Major Depression", Journal of Psychiatric Research, 41(9):801-803, Nov. 2007.

Krahl et al. "Locus Coeruleus Lesions Suppress the Seizure-Attenuating Effects of Vagus Nerve Stimulation", Epilepsia, 39(7):709-714 Jul. 1998.

Kroenke et al. "The PHQ-9 Validity of a Brief Depression Severity Measure", Journal of General Internal Medicine Banner, 16(9): 606-613, Sep. 2001.

Kucewicz et al. "Evidence for Verbal Memory Enhancement with Electrical Brain Stimulation in the Lateral Temporal Cortex", Brain, A Journal of Neurology,141(4); 971-978, Apr. 2018.

Kunugi et al. "Low Serum Cholesterol in Suicide Attempters", 41(2):196-200, Jan. 15, 1997.

Lacassse et al. "Serotonin and Depression: A Disconnect between the Advertisements and the Scientific Literamre", PLOS Mdicine, 2(12): 1211-1216, Dec. 2005.

Leuthardt et al. "A Brain-Computer Interface Using Electrocorticographic Signals in Humans", Journal of Neural Engineering 1(2): 63-71,Jun. 14, 2004.

Lewis et al. "Restoration of Vision in Blind Individuals Using Bionic Devices: A Review with a Focus on Cortical Visual Prostheses", Brain Research,1595: 51-73, Jan. 21, 2015.

LiKamWa et al. "MoodScope: Building a Mood Sensor from Smartphone Usage Patterns", MobiSys '13 Proceeding of the 11th Annual International Conference on Mobile Systems, Applications, and Services: 389-402, Jun. 25-28, 2013.

Liu et al. "Syringe Injectable Electronics", Nature Nanotechnology, 10(7): 629-636, Jul. 2015.

Lozano et al. "Subcallosal Cingulate Gyrus Deep Brain Stimulation for Treatment-Resistant Depression", Biological Psychiatry, 64(6):461-467, Sep. 15, 2008.

Maier et al. "S100B, Homocysteine, Vitamin B12, Folic Acid, and Procalcitonin Serum Levels in Remitters to Electroconvulsive Therapy: A Pilot Study", Disease Markers, 2018: 1-8, Published Online Jan. 10, 2018.

Makris et al. Variability and Anatomical Specificity of the Orbitofrontothalamic Fibers of Passage in the Ventral Capsule/Ventral Striatum (VC/VS): Precision Care for Patient-specific Tractography-Guided Targeting of Deep Brain Stimulation (DBS) in Obsessive Compulsive Disorder (OCD), Brain Imaging and Behavior, 10(4):1054-1067, Dec. 2016.

Malone, Jr. et al. "Deep Brain Stimulation of the Ventral Capsule/Ventral Striatum for Treatment-Resistant Depression", Biological Psychiatry, 65(4):267-275, Feb. 15, 2009.

Manji et al. "The Cellular Neurobiology of Depression", Nature Medicine, 7:541-547, May 1, 2001.

Mann "The Medical Management of Depression",The New England Journal of Medicine, 353:1819-1834, Oct. 27, 2005.

Marangell et al. "Neurostimulation Therapies in Depression: A Review of New Modalities", Acta Psychiatrica Scandinavica, 116(3):174-181, Sep. 2007.

Marangell et al. "Vagus Nerve Stimulation (VNS) for Major Depressive Episodes: One Year Outcomes", Biological Psychiatry, 51(4):280-287, Feb. 15, 2002.

Martin et al. "Brain Blood Flow Changes in Depressed Patients Treated With Interpersonal Psychotherapy or Venlafaxine Hydrochloride", Arch Gen Psychiatry.;58(7):641-648, Jul. 2001.

Mayberg "Limbic-Cortical Dysregulation: A Proposed Model of Depression", Clinical Neurosciences, 9(3), 471-481, 1997.

Mayberg et al. "Deep Brain Stimulation for Treatment-Resistant Depression", Neuron, 45(5):651-660, Mar. 3, 2005.

Mayberg et al. "Reciprocal Limbic-Cortical Function and Negative Mood: Converging PET Findings in Depression and Normal Sadness", The American Journal of Psychiatry, 156(5):675-682, May 1, 1999.

Mayberg et al. "Regional Metabolic Effects of Fluoxetine in Major Depression: Serial Changes and Relationship to Clinical Response", Biological Psychiatry, 48(8):830-843,Oct. 15, 2000.

McCreery et al. "A Characterization of the Effects of Neuronal Excitability Due to Prolonged Microstimulation with Chronically Implanted Microelectrodes", IEEE Transactions on Biomedical Engineering, 44(10):931-939, Oct. 1997.

Merali et al. "Dysregulation in the Suicide Brain: mRNA Expression of Corticotropin-Releasing Hormone Receptors and GABAA Receptor Subunits in Frontal Cortical Brain Region", The Journal of Neuroscience, 24(6): 1478-1485, Feb. 11, 2004.

Milak et al. "Neuroanatomic Correlates of Psychopathologic Components of Major Depressive Disorder", Arch Gen Psychiatry,62(4):397-408, Apr. 2005.

Moessner et al. "Consensus Paper of the WFSBP Task Force on Biological Markers: Biological Markers in Depression", The World Journal of Biological Psychiatry, 8(3):141-174, 2007.

Moran et al. "Motor Cortical Representation of Speed and Direction During Reaching", Journal of Neurophysiology, 82(5): 2676-2692, Nov. 1, 1999.

Morikawa et al. "An Origami-Inspired Ultrastretchable Bioprobe Film Device", IEEE 29th International Conference on Micro Electro Mechanical Systems (MEMS): 149-152, Jan. 2016.

Mueller et al. "Recurrence After Recovery From Major Depressive Disorder During 15 Years of Observational Follow-Up", The American Journal of Psychiatry, 156(7):1000-1006, Jul. 1999.

Muller et al. "Thin-Film, Ultra High-Density Microelectrocorticographic Decoding of Speech Sounds in Human Superior Temporal Gyrus", IEEE Engineering in Medicine and Biology Conference Orlando,6P, Feb. 2016.

(56) References Cited

OTHER PUBLICATIONS

Naples et al. "A Spiral Nerve Cuff Electrode for Peripheral Nerve Stimulation", IEEE Transactions on Biomedical Engineering, 35(11): 905-916, Nov. 1988.
Nemeroff et al. "Elevated Concentrations of CSF Corticotropin-Releasing Factor-Like Immunoreactivity in Depressed Patients", Science, 226(4680):1342-1344, Dec. 14, 1984.
Nemeroff et al. "VNS Therapy in Treatment-Resistant Depression: Clinical Eviedence and Putative Neurobiological Mechanisms", Neuropsychopharmacology, 31:1345-1355, Apr. 19, 2006.
Nestler et al. "Neurobiology of Depression", Neuron, 34(1):13-25, Mar. 28, 2002.
Neuronetics "NeuroStar TMS Therapy® System: FDA-Cleared Transcranial Magnetic Stimulation for Treatment of Depression", Neuronetics, 3 P., Sep. 2, 2011.
Nibuya et al. "Regulation of BDNF and trkB mRNA in Rat Brain By Chronic Electroconvulsive Seizure and Antidepressant Drug Treatments", Journal of Neuroscience, 15(11):7539-7547, Nov. 1, 1995.
Nuttin et al. "Electrical Stimulation in Anterior Limbs of Internal Capsules in Patients with Obsessive-Compulsive Disorder", Lancet, 354,(9189): 1526, Oct. 30, 1999.
Nuvujukian et al. "A Nonhuman Primate Brain-Computer Typing Interface", Proceedings of the IEEE,105(1):66-72, Sep. 12, 2016.
O'Brien et al. "Plasma Cytokine Profiles in DSepressed Patients Who Fail to Respond to Selective Serotonin Reuptake Inhibitor Therapy", Journal of Psychiatric Research, 41(3-4):326-331, Apr.-Jun. 2007.
Ongur et al. "Prefrontal Cortical Projections to the Hypothalamus in Macaque Monkevs", The Journal of Comparative Neurology,401(4):480-505, Nov. 30, 1998.
Oxley et al. "Minimally Invasive Endovascular Stentelectrode Array for High-Fidelity, chronic Recordings of Cortical Neural Activity", Nature Biotechnology, 34: 320-327, Feb. 8, 2016.
Palopoli-Trojani et al. "In Vitro Assessment of Long-Term Reliability of Low-Cost [Mu]ECoG Arrays", 38th Annual International Conference of the IEEE Engineering in Medicine and Biology Society, EMBC, Orlando, FL, USA, Aug. 16-20, 2016, p. 4503-4506, Aug. 16, 2016.
Park et al. "Closed-Loop, Ultraprecise, Automated Craniotomies", Journal of Neurophysiology 113: 3943-3953, Jun. 2015.
Pascual-Marquis et al. "Low Resolution Electromagnetic Tomography: A New Method for Localizing Electrical Activity in The Brain", International Journal of Psychophysiology, 18(1):49-65, Oct. 1994.
Peretti et al. "Safety and Tolerability Considerations: Tricyclic Antidepressants vs. Selective Serotonin Reuptake Inhibitors",Acta Psychiatrica Scandinavica, 101(Suppl.403): 17-25, Sep. 2000.
Petridis et al. "Unobtrusive Low Cost Pupil Size Measurements Using Web Cameras", 2nd International Workshop on Artificial Intelligence and Netmedicine (NetMed'13): 9-20, Nov. 28, 2013.
Piallat et al. "Monophasic But Not Biphasic Pulses Induce Brain Tissue Damage During Monopolar High-Frequency Deep Brain Stimulation", Neurosurgery, 64(1):156-163, Jan. 1, 2009.
Pittenger et al. "Stress, Depression, and Neuroplasticity: A Convergence of Mechanisms", Neuropsychopharmacology, 33:88-109, 2008.
Pool et al. "Psychosurgery in Oler People", Journal of American Geriatrics Society (AGS), 2(7): 456-466, Jul. 1954.
Post et al., "Antidepressant effects of carbamazepine", Journal of Psychiatry, 143(1): 29-34, Jan. 1986.
Quitkin et al. "Study Duration in Antidepressant Research: Advantages of a 12-Week Trial", Journal of Psychiatric Research, 20(3):211-216, Jan. 1, 1986.
Raisman et al. "High-Affinitv 3H-Imipramine Binding in Platelets From Untreated and Treated Depressed Patients Compared to Healthy Volunteers", Psychopharmacology, 75(4):368-371, Dec. 1981.
Raison et al. "Cytokines Sing the Blues: Inflammation and The Pathogenesis of Depression", 27(1):24-31, Jan. 2006.

Rechlin et al. "Are Affective Disorders Associated with Alterations of Heart Rate Variability?", Journal of Affective Disorders,32(4): 271-275, Dec. 1994.
Rubin et al. "Neuroendocrine Aspects of Primary Endogenous Depression", Arch Gen Psychiatry, 44(4):328-336, Apr. 1987.
Ruhe et al. "Mood is Indirectly Related to Serotonin, Norepinephrine and Dopamine Levels in Humans: A Meta-Analvsis of Monoamine Depletion Studies", Molecular Psychiatry, 12:331-359,Jan. 16, 2007.
Rush "About Treatment Resistant Depression", Cyberonics, 2007.
Rush et al. "Vagus Nerve Stimulation (VNS) For Treatment-Resistant Depressions: A Multicenter Study", Biological Psychiatry, 47(4):276-286, Feb. 15, 2000.
Russel "A Circumplex Model of Affect", Journal of Prsonality and Social Psychology, 39(6): 1161-1178, 1980.
Sapolsky "Glucocorticoids and Hippocampal Atrophy in Neuropsychiatric Disorders", Arch Gen Psychiatry. 57(10):925-935, Oct. 2000.
Schalk et al. "Brain-Computer Interfaces Using Electrocorticographic Signals", IEEE Reviews in Biomedical Engineering, 4:140-154, Oct. 17, 2011.
Scherer et al. "Self-Reported Symptoms of Depression and PTSD are Associated with Reduced Vowel Space in Screening Interviews", IEEE Transactions on Affective Computing, 7(1): 59-61, Jan.-Mar. 2016.
Schwartz et al. "Primate Motor Cortex and Free Arm Movements to Visual Targets in Three-Dimensional Space. 1. Relations Between Single Cell Discharge and Direction ofMovement", The Journal of Neuroscience, 8(8): 2913-2927, Aug. 1, 1988.
Seo et al. "Wireless Recording in the Peripheral Nervous System with Ultrasonic Neural Dust", Neuron,91(3): 529-539, Aug. 3, 2016.
Shimizu et al. "Alterations of Serum Levels of Brain-Derived Neurotrophic Factor (BDNF) in Depressed Patients With or Without Antidepressants", Biological Psychiatry, 54(1):70-75, Jul. 1, 2003.
Silk et al. "Pupillary Reactivity to Emotional Information in Child and Adolescent Depression: Links to Clinical and Ecological Measures", The American Journal of Psychiatry, 164(12): 1873-1880, Dec. 2007.
Smith "The Macrophage Theory of Depression", Medical Hypotheses, 35(4):298-306, Aug. 1991.
Smith et al. "A Bayesian statistical analysis of behavioral facilitation associated with deep brain stimulation", Journal of Neuroscience Methods, 183(2):267-276, Oct. 15, 2009.
Solomon et al. "Multiple Recurrences of Major Depressive Disorder", The American Journal of Psychiatry, 157(2):229-233, Feb. 2000.
Speer et al. "Opposite effects of high and low frequency rTMS on regional brain activity in depressed patients", Biological Psychiatry, 48(12): 1133-1141,Dec. 15, 2000.
Sullivan et al. "Genetic Epidemiology of Major Depression: Review and Meta-Analysis", The American Journal of Psychiatry, 157(10): 1552-1562, Oct. 2000.
Sun et al. "Responsive Cortical Stimulation For The Treatment of Epilepsy", Neurotherapeutics,5(1):68-74, Jan. 2008.
Taylor et al. "Direct Cortical Control of 3D Neuroprosthetic Devices", Science, 296, (5574):1829-1832, Jun. 7, 2002.
Troncoso et al. "Vision's First Steps: Anatomy, Physiology, and Perception in the Retina, Lateral Geniculate Nucleus, and Early Visual Cortical Areas", Visual Prosthetics: 23-57, Jan. 4, 2011.
Tung et al. "Using Finite State Automata To Produce Self-Optimization and Self-Control", IEEE Transactions on Parallel and Distributed Systems, 7(4):439-448, Apr. 1996.
Turner et al. "Selective Publication of Anti-Depressant Trials and its Influence on Apparent Efficacy", The New England Journal of Medicine, 358:252-260, Jan. 17, 2008.
Van Rijsbergen et al. "Can a One-Item Mood Scale Do the Trick? Predicting Relapse over 5.5-Years in Recurrent Depression", PLOS One, 7(10):1-5, Oct. 3, 2012.
Velasco et al. "Neurobiological Background for Performing Surgical Intervention in the Inferior Thalamic Peduncle for Treatment of Major Depression Disorders", Neurosurgery, 57(3):439-448, Sep. 1, 2005.

(56) References Cited

OTHER PUBLICATIONS

Viventi et al. "Flexible, Foldable, Actively Multiplexed, High-Density Electrode Array for Mapping Brain Activity In Vivo", Nature Neuroscience, 14(12): 1599-1605, 2011.
Wang et al. "An Electrocorticographic Brain Interface in an Individual with Tetraplegia", PLOS One 8(2):1-8, Feb. 6, 2013.
Watanabe et al. "Transcranial Electrical Stimulation Through Screw Electrodes For Intraoperative Monitoring of Motor Evoked Potentials", Journal of Neurosurgery 100(1):155-160, Jan. 1, 2004.
Wells et al. "The Functioning and Well-Being of Depressed Patients: Results From the Medical Outcomes Study", JAMA, 262(7):914-919, Aug. 18, 1989.
Wheeler et al. "An Implantable 64-Channel Neural interface With Reconfigurable Recording and Stimulation", 37th Annual International Conference of the IEEE Engineering in Medicine and Biology Society (EMBC), 7837-7840, Aug. 2015.
Wodlinger et al. "Ten-Dimensional Anthropomorphic Arm Control in a Human Brain-Machine Interface: Difficulties, Solutions, and Limitations", Journal of Neural Engineering, 12(1):1-17, Dec. 16, 2014.
Wong et al. "Closed-Loop Control of Cellular Functions Using Combinatory Drugs Guided By a Stochastic Search Algorithm", Proceedings of the National Academy of Sciences, 105(13): 5105-5110, Apr. 1, 2008.
Xie et al. "Three-Dimensional Macroporous Nanoelectronic Networks as Minimally Invasive Brain Probes", Nature Materials,14: 286-1292 Oct. 5, 2015.
Yamagiwa et al. "Flexible Parylene-Film Optical Waveguide Arrays", Applied Physics LKetters,107(8), 6P, 2015.
Yamagiwa et al. "Self-Curling and -Sticking Flexible Substrate for ECoG Electrode Array", IEEE 26th International Conference on Micro Electro Mechanical Systems (MEMS): 480-483, Jan. 2013.
Yanagisawa et al. "Electrocorticographic Control of a Prosthetic Arm in Paralyzed Patients", Annals of Neurology,71(3): 353-361, Mar. 2012.
Yirmiya et al. "Illness, Cytokines, and Depression", Annals of the New York Academy of Sciences, 917(1):478-487, Jan. 2000.
Yousry et al. "Localization of the Motor Hand Area to a Knob on the Precentral Gyrus, A New Landmark", Brain, 120(1): 141-157, Jan. 1, 1997.
Zhou et al. "Pulvinar-Cortex Interactions in Vision and Attention", Neuron, 89(1):209-220, Jan. 6, 2016.
International Search Report and the Written Opinion dated Jun. 23, 2021 From the International Searching Authority Re. Application No. PCT/IB2021/050253. (21 Pages).
Invitation to Pay Additional Fees, Communication Relating to the Results of the Partial International Search and the Provisional Opinion dated May 3, 2021 From the International Searching Authority Re. Application No. PCT/IB2021/050253. (10 Pages).
Notice of Reason(s) for Rejection dated Nov. 2, 2021 From the Japan Patent Office Re. Application No. 2019-533071 and its Translation into English. (9 Pages).
Supplementary European Search Report and the European Search Opinion dated Feb. 16, 2022 From the European Patent Office Re. Application No. 19820226.9. (8 Pages).
Grounds of Reason of Rejection dated May 26, 2022 From the Korean Intellectual Property Office Re. Application No. 2010-7029927. (3 Pages).
Official Action dated Jul. 8, 2022 from US Patent and Trademark Office Re. U.S. Appl. No. 16/954,554. (69 pages).
Official Action dated Jun. 8, 2022 from US Patent and Trademark Office Re. U.S. Appl. No. 16/469,165. (78 pages).

* cited by examiner

VIRTUAL USER INTERFACE SYSTEM AND METHODS FOR USE THEREOF

RELATED APPLICATIONS

This application is a National Phase of PCT Patent Application No. PCT/IB2019/054948 having Internation filing date of Jun. 13, 2019, which claims the benefit of priority under 35 USC § 119(e) of U.S. Provisional Patent Application No. 62/684,756 filed on Jun. 14, 2018. The contents of the above applications are all incorporated by reference as if fully set forth herein in their entirety.

FIELD AND BACKGROUND OF THE INVENTION

The present application, in some embodiments thereof, relates to systems and methods for providing a virtual user interface, more particularly, but not exclusively, to systems for providing a virtual user interface by stimulating the visual cortex of a person.

Brain computer interfaces (BCIs) are devices or systems used for interacting with the brain and other types of neural tissues for performing sensing and/or recording of neuronal tissues and for stimulating neurons in such tissues. Such BCIs may be used for sensing/recording signals (typically, transient electrical signals such as voltage or current signals) associated with neuronal activity. Currently, most BCIs include multiple electrically conducting electrodes, often arranged as a two dimensional (2D) or three-dimensional (3D) electrode arrays. Such electrode arrays may be used to sense electrical signals associated with neuronal activity and/or stimulate neurons by passing suitable electrical currents through the electrodes.

Some electrodes or electrode sets included in BCIs may be non-invasive such as, for example extra-cranial EEG electrode arrays, while other electrodes or sets of electrodes may be invasive such as flexible intracranial electrocorticogram electrode arrays placed on the cortical surface. Other invasive electrode arrays may be inserted into the cortical tissue (such as, for example Utah arrays which may be typically placed on the cortical surface and inserted superficially into the first few millimeters of cortical tissue). Still other electrode arrays may be disposed on stents. Such stents may be inserted through the vasculature using minimally invasive methods, and may be disposed in blood vessels of the brain close to relevant brain regions.

The signals sensed and/or recorded by electrode set(s) of the BCI systems of the present applications may include, inter alia, single neuron extracellular recorded action potentials (spikes), extracellular recorded neuronal action potentials from single or multiple neurons, local field potentials (LFP) from single or multiple neurons, surface recorded field potentials resulting from summed activity of neuronal assemblies, Ecog signals and extra-cranially recorded EEG signal.

Significant advances have been recently achieved in the use of such BCIs used for sensing/recording and/or stimulation for sensing/recording neural activity from the motor cortex and processing the sensed signals to control the operation/movements of a prosthesis replacing a missing limb in patients. Advances were also made in using signals recorded from the motor cortex of quadriplegic patients to enable such patients to control a motorized wheelchair or to control other devices such as a computer which may perform various functions for assisting such patient.

Other uses for such BCIs for assisting blind patients include using images of a field of view acquired by an external video camera and processed to control electrical stimulation of the primary visual cortex of the blind patient by a flexible Ecog electrode array BCI placed on the surface of the visual cortex, resulting in the perception of phosphenes by the blind patient which may assist patient's navigation, object identification and obstacles avoidance.

Graphic user interfaces (GUI) are visual interfaces that may be presented to a user on a suitable display device and may serve, inter alia, for presenting information to a user and for enabling the user to interact with the presented GUI for performing and/or controlling a computational task. Such GUIs are ubiquitous in many computer systems and may operate by presenting an image on the screen of a computer or laptop or other hand held or mobile devices (for example a smartphone). The image may be graphical and may or may not include alphanumeric symbols. A common example is a "dialog box" presented on the computer display that presents multiple choices to the user. The user may select one or more choices on such a dialog box and the selection may be used as input to the computer program operating on the computer for controlling the operation of the program.

The interaction with a GUI may be performed by the user operating a pointing device (such as, for example, a mouse, a light pen and the like) to move a cursor on the screen and click on a selected some of the options as is well known in the art. In other systems, a touch sensitive display screen may be used for the interaction by the user directly touching the touch sensitive screen.

Some other GUIs are presented to a user by using a heads up display (HUD), such as the HUD helmets used by fighter plane pilots. Such HUD systems have the advantage that they move with the head of the user, enabling the user to freely direct his/her gaze while still keeping the GUI in their visual field of view (FOV). Similarly, many virtual reality (VR) and augmented reality (AR) systems include a display device worn on the head of the user, such as, for example VR goggles or similar VR or AR eyeglasses that may display information and one or more GUIs to the user. More sophisticated VR/AR systems may allow the user to interact with the GUI by tracking and interpreting the user's hand movements (by using suitable sensors) for performing computational tasks and for interacting with a program and/or controlling the operation of the program.

One limitation of some of the above systems is that they require a display device (such as a computer screen or a touch sensitive screen or the miniaturized screens in the head worn VR/AR goggles or glasses. Such devices may be relatively expensive and may also require the user to look at the display for performing the interaction with the GUI limiting the user's ability to observe his/her visual environment.

While HUD and VR/AR systems adequately address the above limitation they require the constant wearing of a helmet or goggles which may be awkward and inconvenient for medium and long use periods, and may also be unacceptable or frowned upon when socializing with other people.

SUMMARY OF THE INVENTION

There is also provided, in accordance with some embodiments of the systems of the present application, a virtual user interface system. The system includes one or more stimulating devices for stimulating neurons in one or more regions of the visual cortex of the user to present to the user a perceived virtual image responsive to the stimulating. The system also includes one or more sensing devices for sensing signals associated with neuronal activity in one or more regions of the motor and/or pre-motor cortex of the user. The system also includes at least one processor/controller suitably coupled to the one or more stimulating devices and to the one or more sensing devices. The processor/controller is programmed for stimulating one or more selected regions of the visual cortex of the user to present to the user a perceived virtual image responsive to the stimulating. The processor controller is also programmed to sense signals from the one or more regions of the motor and/or pre-motor cortex of the user, the sensed signals resulting from the user performing a movement and/or intending to perform a movement and/or imagining the performing of a movement to interact with the presented virtual image. The processor/controller is also programmed to process the sensed signals to obtain computed data indicative a user's interaction with the presented virtual image, and to perform a general computing task responsive to the computed data. The system also includes a power source for providing power to the system. In accordance with some embodiments of the system, the one or more stimulating devices are one or more stimulating electrode set(s) or one or more light emitting devices.

In accordance with some embodiments of the system, the one or more light emitting devices are selected from one or more lasers, one or more light emitting diodes, one or more diode lasers, one or more quantum dots, one or more light emitting diode arrays, one or more laser diode arrays, one and more quantum dot arrays, and any combinations thereof.

In accordance with some embodiments of the system, the one or more sensing devices are selected from one or more sensing electrode set(s) and one or more light sensitive devices.

In accordance with some embodiments of the system, the one or more light sensitive devices are selected from, one or more photosensors, one or more photosensor arrays, one or more photodiodes, one or more photodiode arrays, one or more phototransistors, one or more phototransistor arrays, a multi-pixel CMOS imaging array, a CCD array imager and any non mutually exclusive combinations thereof.

There is also provided, in accordance with the methods of the present application, a method for using a virtual user interface. The method includes the steps of:

1) Stimulating one or more selected regions of the visual cortex of the user to present to the user a perceived virtual image responsive to the stimulating.

2) Sensing signals from one or more regions of the motor and/or pre-motor cortex of the user, the sensed signals are associated with the user performing a movement and/or intending to perform a movement and/or imagining the performing of a movement to interact with the presented virtual image.

3) Processing the sensed signals to obtain data representing a user interaction with the virtual image, and 4) Performing a general computing task responsive to the data.

In accordance with some embodiments of the methods, the step of sensing is selected from the steps of: 1) sensing electrical signals from one or more regions of the motor and/or pre-motor cortex of the user, or 2) sensing optical signals from one or more regions of the motor and/or pre-motor cortex of the user.

In accordance with some embodiments of the methods, the step of stimulating is selected from the following steps:

1) Optically stimulating one or more selected regions of the visual cortex of the user to present to the user a perceived virtual image responsive to the stimulating, or, 2) Electrically stimulating one or more selected regions of the visual cortex of the user to present to the user a perceived virtual image responsive to the stimulating.

There is also provided, in accordance with some embodiments of the systems of the present application, a virtual user interface system. The system includes one or more stimulating electrode sets including a first plurality of electrodes for electrically stimulating one or more regions of the visual cortex of the user to present to the user a perceived virtual image responsive to the stimulating. The system also includes one or more sensing electrode sets including a second plurality of electrodes for sensing electrical signals in one or more regions of the motor and/or pre-motor cortex of the user. The system also includes at least one processor/controller suitably electrically coupled to the one or more stimulating electrode sets and to the one or more sensing electrode sets. The processor/controller is programmed for electrically stimulating one or more selected regions of the visual cortex of the user to present to the user a perceived virtual image responsive to the stimulating. The processor/controller is also programmed for sensing electrical signals from the one or more regions of the motor and/or pre-motor cortex of the user, the sensed signals resulting from the user performing a movement and/or intending to perform a movement and/or imagining the performing of a movement to interact with the presented virtual image. The processor controller is programmed to process the sensed signals to obtain computed data indicative a user interaction with the presented virtual image, and to perform a general computing task responsive to the computed data. The system also includes a power source for providing power to the system.

In accordance with some embodiments of the system, the one or more stimulating electrode sets and/or the one or more sensing electrode sets are selected from, an electrode array, an Ecog electrode array, a UTAH electrode array, an injectable electrode array, a mesh implantable electrode array, a flexible electrode array, a foldable electrode array, neural dust, a stentrode array and any combinations thereof.

In accordance with some embodiments of the system, the perceived image is an image selected from, an image comprising one or more geometrical shapes, an image comprising alphanumerical text, an image comprising one or more colored regions, an image comprising one or more lines, and any non-mutually exclusive combinations thereof.

In accordance with some embodiments of the system, the general computing task is a computing task requiring input from the user for the operation thereof.

In accordance with some embodiments of the system, the at least one processor/controller is programmed to perform the processing of the electrical signals sensed in one or more regions of the motor and/or pre-motor cortex of the user by computing one or more parameters of the movement performed by the user and/or imagined by the user and using the one or more parameters to determine if the intended end target of the imagined movement and/or the performed movement falls within or in the vicinity of a perceived virtual image presented to the user by the stimulating.

In accordance with some embodiments of the system, the one or more sensing electrode sets and the one or more stimulating electrode sets are selected from: 1) a single electrode array including the one or more stimulating electrode set and the one or more stimulating electrode set, and 2) at least one electrode array including the one or more stimulating electrode sets and at least one electrode array including the one or more sensing electrode set(s).

In accordance with some embodiments of the system, the at least one processor/controller is programmed to control, based on the user's interactions with the virtual image, the operation of one or more devices, the one or more devices are selected from devices external to the body of the user, devices implanted in the user's body and devices worn by or attached to the user.

In accordance with some embodiments of the system, the one or more devices is selected from one or more sensors, one or more effectors, an effector device attached to or carried by the user, an effector device carrying the user, a prosthesis, a motorized vehicle, a land vehicle, an airborne vehicle, a marine vehicle, an effector device in the vicinity of the user, a remote effector device, a drone, a motorized exoskeleton device carrying the user, a robotic device operable by the user, a sound source, an ultrasound source, an audio speaker, a visible light source, an IR light source, a device for therapeutically treating the user, a diagnostic device, an augmented reality (AR) headset and any non-mutually exclusive combinations thereof.

In accordance with some embodiments of the system, the one or more sensing electrode sets are configured to be disposed on or within or in the vicinity of, the primary motor cortex, the pre-motor cortex, BA4, the precentral gyms, the supplementary motor cortex (SMC), BA6, and any combinations thereof.

In accordance with some embodiments of the system, the one or more stimulating electrode sets are configured to be disposed on or within or in the vicinity of, the primary visual cortex (V1), striate cortex, the supplementary visual cortex, the secondary visual cortex (V2), the prestriate cortex, the cortical visual area 4 (V4), the medial temporal (MT) lobe of the visual cortex (V5), the dorsomedial (DM) visual area (V6), BA17, BA 18 and BA19 and any combinations thereof.

In accordance with some embodiments of the system, the at least one processor/controller is selected from, a microprocessor, a microcontroller, a CPU, a GPU, a DSP, a cluster of processors, a parallel computing network, a quantum computing device, a quantum computer, and any combinations thereof.

There is therefore provided, in accordance with some embodiments of the methods of the present application, a method for using a virtual user interface, the method includes the steps of: electrically stimulating one or more selected regions of the visual cortex of the user to present to the user a perceived virtual image responsive to the stimulating, sensing electrical signals from one or more regions of the motor and/or pre-motor cortex of the user, the sensed signals are associated with the user performing a movement and/or intending to perform a movement and/or imagining the performing of a movement to interact with the presented virtual image, processing the sensed signals to obtain data representing a user interaction with the virtual image, and performing a general computing task responsive to the data.

In accordance with some embodiments of the methods, the step of performing is selected from, performing a selection, performing a decision, and providing quantitative information. In accordance with some embodiments of the methods, the step of electrically stimulating comprises stimulating one or more of, the primary visual cortex (V1), striate cortex, the supplementary visual cortex, the secondary visual cortex (V2), the prestriate cortex, the cortical visual area 4 (V4), the medial temporal (MT) lobe of the visual cortex (V5), the dorsomedial (DM) visual area (V6), BA17, BA 18 and BA19.

In accordance with some embodiments of the methods, the step of sensing electrical signals includes sensing electrical signals in one or more of, the primary motor cortex, the pre-motor cortex, BA4, the precentral gyms, the supplementary motor cortex (SMC), BA6, and any combinations thereof.

In accordance with some embodiments of the methods, the method also includes the step of controlling the operation of one or more devices responsive to the interaction of the user with the presented virtual image.

In accordance with some embodiments of the methods, the step of processing the sensed signals includes computing from the sensed signals one or more parameters of a movement performed by the user and/or imagined by the user and using the one or more parameter to determine if the intended end target of the imagined movement and/or the performed movement falls within or in the vicinity of a perceived virtual image presented to the user by the stimulating.

In accordance with some embodiments of the methods, the general computing task comprises operating a browser program for presenting one or more virtual images comprising alphanumeric data and/or graphic content and/or, text, and/or video images to the user by directly stimulating of the visual cortex of the user.

In accordance with some embodiments of the methods, the general computing task comprises a program for operating one or more devices.

In accordance with some embodiments of the methods, the one or more devices are selected from one or more sensors, one or more effectors, an effector device attached to or carried by the user or worn by the user, an effector device carrying the user, a prosthesis, a motorized vehicle, a land vehicle, an airborne vehicle, a marine vehicle, an effector device in the vicinity of the user, a remote effector device, a drone, a motorized exoskeleton device carrying the user, a robotic device operable by the user, a sound source, an ultrasound source, an audio speaker, a visible light source, an IR light source, a device for therapeutically treating the user, a diagnostic device, an augmented reality headset, and any non-mutually exclusive combinations thereof.

In accordance with some embodiments of the system, the one or more sensing electrode sets and the one or more stimulating electrode sets are intracalvarial electrodes implanted within the calvarial bone of a skull of the user.

In accordance with some embodiments of the system, the one or more sensing electrode sets and the one or more stimulating electrode sets are intracalvarial electrodes implanted within the calvarial bone of a skull of the user overlying one or more regions of the visual cortex of the user.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention may involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings (in which like components are designated by like reference numbers) makes apparent to those skilled in the art how embodiments of the invention may be practiced.

In the drawings.

DETAILED DESCRIPTION OF SPECIFIC EMBODIMENTS OF THE INVENTION

Abbreviations

Figure 1:
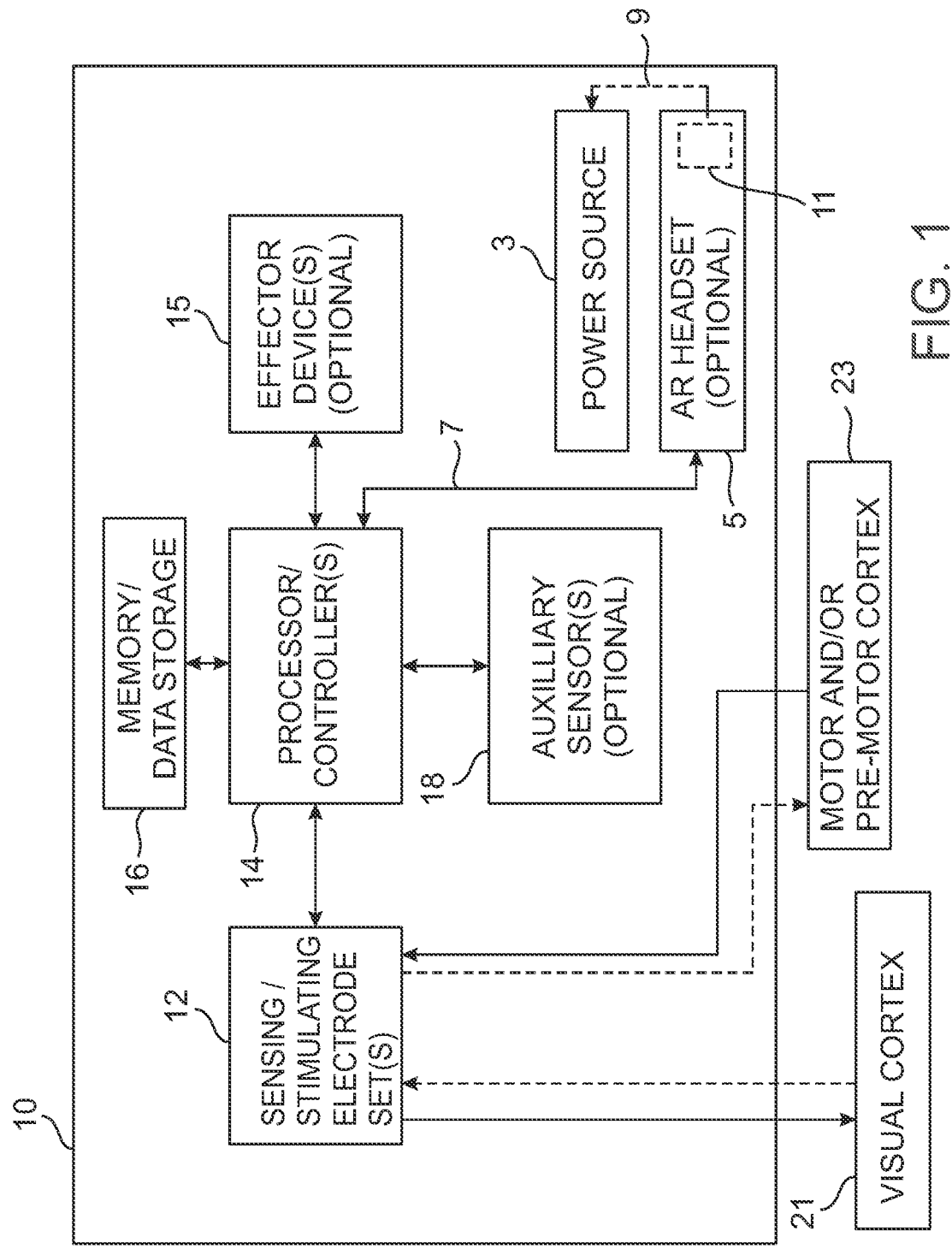
FIG. 1 is a schematic block diagram illustrating the components of a general user interface system, in accordance with some embodiments of the user interface systems of the present application.

The following abbreviations are used throughout the present application:

| ABBREVIATION | MEANING |
| --- | --- |
| BA | Broadman Area |
| BCI | Brain computer interface |
| CPU | Central processing unit |
| AR | Augmented reality |
| DM | Dorso medial |
| DSP | Digital signal processor |
| Ecog | Electrocorticogram |
| ECOG array | Electrocorticographic electrode array |
| EEG | Electroencephalogram |
| EEPROM | Erasable electronically programmable ROM |
| EPROM | electronically programmable |
| FOV | Field of view |
| GPU | Graphic processor unit |
| GUI | Graphic user interface |
| HUD | Heads up display |
| IC | Integrated circuit |
| IMA | Inertial measurement unit |
| IR | Infrared |
| LAN | Local area network |
| LFP | Local field potential |
| LGN | Lateral geniculate nucleus |
| MT | Mid temporal |
| RAM | Random access memory |
| ROM | Read only memory |
| SMA | Supplementary motor area |
| UV | Ultraviolet |
| VPN | Virtual private network |
| VR | Virtual reality |
| WAN | Wide area network |

The present invention, in some embodiments thereof, relates to systems and devices for providing a graphic user interface (GUI) to a user, and more specifically to systems and devices for presenting a virtual GUI to a user by stimulating the visual cortex and sensing electrical activity in the pre-motor cortex and/or motor cortex of the user to detect interactions of the user with the virtual GUI.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. It is expected that during the life of a patent maturing from this application many relevant devices and systems for sensing/recording cortical electrical activity and for stimulating the cortex will be developed and the scope of the terms "sensing" "recording" and "stimulating" are intended to include all such new technologies a priori. As used herein the term "about" refers to ±10%. The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The term "virtual image" is used throughout the application and the claims to denote an image that is perceived by a user as a result of direct stimulation of one or more regions of the visual cortex.

The term "virtual GUI" is used throughout the application and the claims to denote a GUI that comprises one or more images that is/are perceived by a user as a result of direct stimulation of one or more regions of the visual cortex.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It has serendipitously occurred to the inventor of the present invention that it may be possible to overcome some of the limitations of the GUI systems described in the background section hereinabove by using suitable stimulation of the visual cortex or parts thereof to result in the user perceiving an image of a virtual user interface in the FOV of the user. The user may interact with the perceived virtual image by either moving a limb (preferably, but not obligatorily a hand) in a direction of a region of the virtual image or by intending to move the limb or by mentally imagining the moving the limb (without actually moving the limb. Suitable sensing electrodes may then be used to sense electrical signals evoked in one or more regions of the pre-motor cortex and/or the motor cortex of the user. The sensed signals (associated with the limb movement and/or with the intention to move the limb) may then be processed and decoded to provide the desired interaction with the virtual GUI as disclosed in detail hereinafter. This system and methods of operation and use thereof eliminate the need to present a GUI to the user on a physical display device and may also advantageously enable the presenting of information (either textual/alphanumeric or by using images) to the user without the need for a physical display device.

Reference is now made to FIG. 1 which is a schematic block diagram illustrating the components of a general user interface system, in accordance with some embodiments of the user interface systems of the present application.

The system 10 includes one or more sensing/stimulating electrode set(s) 12, which are in communication with one or more processor/controller(s) 14. The processor/controller(s) 14 may be suitably connected to one or more memory and/or data storage devices 16 for storing and retrieving data.

In accordance with some embodiments of the system, the sensing/stimulating electrode set(s) 12 may be included in a single electrode set. In accordance with other embodiments of the system, the sensing/stimulating electrode set(s) 12 may include two or more physically separate electrode sets.

For example, in some embodiments, the sensing/stimulating electrode set(s) 12 may be implemented as a first sensing electrode set for stimulating one or more regions of the visual cortex of the user and a second electrode set (separate from the first set) for sensing electrical signals in one or more parts of the pre-motor cortex and/or the motor cortex of the same user. In another embodiment of the system, a single electrode array or electrode set comprising multiple electrodes may be used such that a first sensing electrode subset may be used for stimulating one or more regions of the visual cortex of the user and a second electrode subset of the same single electrode array or electrode set for sensing electrical signals in one or more parts of the pre-motor cortex and/or the motor cortex of the same user.

The processor/controller(s) 14 may be one or more computing devices selected from, one or more processor/controller external to the cranium of the user, one or more intracranial processor/controller, at least one wearable processor/controller, at least one remote processor/controller, at least one digital signal processor (DSP), at least one graphic processing unit (GPU), at least one quantum computing device, a central processing unit (CPU), or any combinations of the above. In some embodiments, the processor/controller(s) 14 may include and/or emulate a neural network. For example, the processor/controller(s) 14 may include or may be connected to one or more neuromorphic ICs. Alternatively and/or additionally, the processor/controller 14 may be programmed to emulate one or more neural networks by software operative on the processor/controller(s) 14.

Furthermore, the processor/controller 14 may have access to the "cloud" via the internet (preferably, wirelessly, but also possibly in a wired way) or through any other type of network, such as, for example, a LAN, a WAN, a VPN or any other type of wired or wirelessly accessible network.

In some embodiments, the processor/controller(s) 14 may include wireless communication circuits, such as Bluetooth, or WiFi communication units or circuits (not shown in detail in FIG. 1 for the sake of clarity of illustration). Such wireless communication means may enable the processor/controller to wirelessly communicate with external devices, such as for example, a remote computer, a server, a cellular telephone, or any other type of. Such embodiments may be useful in cases in which the processing power of the processor/controller(s) 14 is limited. Such embodiments may allow the offloading of some or all of the computational burden to other processing devices, such as remote computer(s), servers, a cluster of computers or any other suitable computing devices, and may enable the use of cloud computing, or parallel computing for processing the data recorded/sensed reducing the computational load on the processor/controller(s) 14. The results of such off loaded computations may then be returned or communicated (preferably wirelessly) to the processor/controller 14 and used for performing the controlling of the sensing and/or stimulation of the appropriate brain structures as disclosed herein.

Preferably, for invasive systems, the processor/controller(s) 14 are microminiaturized to have the smallest possible size and to minimize power requirements and heat output. However, if wearable computing devices or similar external computers devices are being used, the size and power requirement of the computing devices may be increased.

The processor/controller(s) 14 and/or the one or more sensing/stimulating electrode set(s) 12 may include any necessary electrical circuitry (not shown for the sake of clarity of illustration) required for conditioning, and/or amplifying, and/or filtering and/or digitizing the electrical signals sensed by the one or more sensing/stimulating electrode set(s) 12 (such as, for example, an analog to digital converter (ADC), signal amplifiers, analog filters, digital filters or any other suitable electrical and/or electronic or opto-electronic circuitry).

The system 10 may also include any electrical circuitry (some of the electrical and/or electronic circuitry is not shown for the sake of clarity of illustration) for providing electrical stimulation to nervous tissues through the one or more sensing/stimulating electrode set(s) 12 as is known in the art. Such electrical circuitry may include, such as one or more current sources, multiplexing circuitry, one or more electrical pulse generators, timing circuitry and any other electrical circuitry necessary for stimulating neurons through one or more of the sensing/stimulating electrode set(s) 12.

The system 10 also includes a suitable power source 3 (preferably, an electrical power source) for energizing the processor controller(s) 14, the memory/data storage 16 and any other components of the system 10 requiring power.

It is noted that in any of the system embodiments disclosed herein and illustrated in the drawing figures in which the processor/controller(s) 14 is shown to be directly connected to one or more stimulating electrode sets (or sensing and stimulating electrode set(s)) without explicitly showing or illustrating such stimulating circuitry it is to be understood that such circuitry (such as, for example, one or more current sources, multiplexing circuitry, one or more electrical pulse generators, timing circuitry and any other electrical circuitry necessary for stimulating neurons through one or more of the sensing/stimulating electrode sets) may be included in the processor/controller(s) 14 and is not shown in detail for the sake of clarity of illustration.

It is also noted that the power lines connecting the power source 3 to any power requiring components are not shown in any of FIGS. 1-6 hereinafter, for the sake of clarity of illustration.

The system 10 may also (optionally) include one or more auxiliary sensors 18 suitably connected and coupled to the processor/controller(s) 14. The optional auxiliary sensors 18 may include one or more sensors selected from an imaging sensor, a monochrome imaging sensor, a color imaging sensor, an infrared (IR) imaging sensor, an ultraviolet (UV) imaging sensor, an ionizing radiation sensor, a Geiger counter, a microphone, a stereoscopic depth sensor, an inertial measurement unit (IMU), one or more accelerometers, a vibrometer, a temperature sensor, a microphone, an acoustic sensor for sensing sound and/or infrasound and/or ultrasound, a thermistor, a sensor for sensing and/or detecting volatile compounds in air, and any combinations thereof.

The auxiliary sensors 18 may also include one or more sensors for measuring a physiological signal of the user, such as, for example, a medical sensor, a blood pressure sensor, a perspiration sensor, an eye-tracking device, and a pupillometry device (for measuring gaze direction and/or pupil diameter or size).

The auxiliary sensors 18 may include sensors (such as, for example, a camera or stereoscopic depth sensor, or laser range finder) that may provide the processor/controller(s) 14 with sensed data usable for providing the user with geo-contextual information or data, (such as the position of various real objects or of the user's body or body parts in space and/or relative to other objects in the environment).

The system 10 may also (optionally) include one or more effector devices 15. The effector devices 15 may be effector devices implanted within the body of the user, but may also be external effector devices carried by the user and/or worn by the user (such as, for example a AR headset or goggles) and/or externally attached to the body of the user or to one or more garment worn by the user on the body. The effector devices 15 may also be any type of external effector device placed anywhere and remotely and wirelessly controllable and/or wirelessly operable by the user that is using the system 10. The effector device(s) 15 may be effector device attached to or carried by or worn by the user, an effector device carrying the user, a prosthesis, a motorized vehicle, a land vehicle, an airborne vehicle, a marine vehicle, an effector device in the vicinity of the user, a remote effector device, a drone, a motorized exoskeleton device carrying the user, a robotic device operable by the user, a sound source, an ultrasound source, an audio speaker, a visible light source, an IR light and an augmented reality (AR) headset. The effector device(s) 15 may also include any non-mutually exclusive combinations of the above described effectors.

In accordance with some embodiments, the effector device(s) may be be selected from, a device for controllably delivering a substance or a composition to the body of the user or to a selected part of the body, a device for medically and/or therapeutically treating the body of the user and/or any combinations thereof. The substance or composition may be selected from, a drug, a therapeutic agent, a stimulant, a sedative, an anti-inflammatory agent, a muscle relaxing agent, an antibacterial agent, an antifungal agent, an antiviral agent, a nutrient, a hormone, a neurotransmitter, a neuro-protective agent, a vitamin, an anticoagulant agent, or and any non-mutually exclusive or medically contraindicated combinations of the above described substances.

Some of the effector devices may be therapeutic devices for medically and/or therapeutically treating the body of the user and may be selected from, a device for delivering electrical stimulation to said body or to a part thereof, a device for heating or cooling said body or a selected region or organ thereof, a device for delivering therapeutic electromagnetic radiation to said body or to a part thereof, and any combinations thereof.

The system 10 may also (optionally) include an Augmented reality (AR) headset 5. The AR headset 5 may be any type of AR device/headset known in the art and may provide the user all the augmentation features of AR devices. The AR headset 5 may be in communication with the processor/controller(s) 14 in a wired or wireless manner. For example, the AR headset 5 may have one or more leads 7 electrically coupling the processor/controller(s) to the AR headset 5 (as illustrated in FIG. 1). It is noted that the AR headset 5 may be (optionally) connected to the power source 3 by suitable leads 9 to provide power to any of the components of the system 10. Alternatively, a power source 11, included in the AR headset 5 may make the power source 3 redundant as the power source 11 of the AR headset 5 may provide all the power required by the system 10. This may have an advantage because the power source 11 of the AR headset 5 may be much larger and have a better charge capacity than any power source implanted intracranially in the head of the user, and may be much easier to replace than an intracranially implanted power source. However, such a power source may have to be properly electrically coupled to any intracranial implanted parts of the system by suitable leads (such as for example the leads 7).

Alternatively, the AR headset maybe wirelessly connected to the processor/controller (as disclosed in detail in FIGS. 4-6 hereinafter). It is noted that such an AR device or headset may be (optionally) included in any of the systems disclosed in the present application as included in the effector device(s) 15.

The memory/data storage device(s) 16 may be any type of memory and/or data storage device(s) known in the art for storing and/or retrieving data. Non limiting, exemplary memory and/or data storage devices usable in the system 10 (and in any of the other cognition augmenting/enhancing systems disclosed hereinafter), may include one or more devices such as ROM, RAM, EPROM, EEPROM, Flash memory devices of any type known in the art, optical memory and/or storage devices and any combinations thereof.

The sensing/stimulating electrode set(s) 12 may be implemented as different types of electrodes set(s) or electrode group(s). Such different electrode set(s) are well known in the art and several forms of such Electrode set(s) are commercially available on the market. The structure and operation of such electrode set(s) is well known in the art, and is therefore not described in detail hereinafter. Briefly, the Electrode set(s) 12 may be selected from, a Multi-electrode sets, an electrode array for penetrating the surface of the cortex, a stent type electrode array for insertion into a blood vessel within the brain, a flexible multi electrode array for recording from and/or stimulation of one or more surfaces of the brain, including but not limited to cortical regions and/or other brain surface regions for recording and/or stimulation thereof, flexible mesh-type electrode arrays for internal implantation within cortical regions and/or cortical layers, flexible mesh type electrode arrays that may be placed on the cortical surface, and any combinations of the above electrode and electrode set(s) types.

It is noted that in accordance with some embodiments of the systems of the present application, the stimulating/sensing electrode set(s) disclosed in the present application may be intracranially surgically implanted (either epidurally or subdurally), but may also be implanted minimally invasively within the cranial bone or the calvarial bone of the skull of the user. For example, any of the electrode sets used for stimulating and or sensing may be implanted within the diploe of the calvarial bone of the user such that they are disposed between the outer table and the inner table of the calvarial bone. This may be achieved by making an opening in the outer table of the calvarial bone (preferably, but not obligatorily, in the part of the calvarial bone overlying the visual cortex for the stimulating electrode set(s) and in the part of the calvarial bone overlying the motor and/or pre-motor cortex for the sensing electrode set(s)), and making a space in the calvarial cancellous bone layer reaching all the way to the inner table (but without fully penetrating the inner table) by removing the cancellous bone layer (and, optionally removing, part of the outer table, taking precautions not to fully penetrate or breach the inner table). An implant including the relevant (stimulating or sensing) electrode set(s) may then be inserted into formed space through the opening in the outer table and the implant may then be sealed in place. Preferably, the electrodes of the electrode sets are placed in contact with the exposed upper surface of the inner table of the calvarial bone in order to reduce the distance between the electrodes and the relevant cortical region underlying the unbreached inner table. This may advantageously reduce the amount of material intervening between the electrodes and the cortex and increase the signal to noise ratio of the recording and also reduce the amount of current necessary to stimulate the cortical tissues underlying the (stimulating) electrodes.

Using such intracalvarial electrode set placement may have the advantages of being less invasive than implantation of intracranial electrode sets with the concomitant reduction to patient risks, and may also be quite simple and cost effective as compared to a full craniotomy exposing the cortex. Such simple implantation procedures may therefore be performed quickly in outpatient clinics substantially reducing cost and patient discomfort and eliminating the need for patient hospitalization (as may be required after trans-cranial craniectomy exposing the brain).

The methods for construction and for of use of such diverse types of electrode types and their associated electronic circuits, usable in the enhanced/augmented/improved cognition systems, as well as methods and algorithms for processing sensed neuronal activity to generate commands for controlling effector devices (including prosthetic limbs) or to perform various computations (both analog and/or digital) for pattern recognition and/or pattern detection and/or pattern classifications, and/or to perform other general computational tasks are well known in the art and are described in detail, inter alia, in some of the following references:

1. Jeneva A. Cronin, Jing Wu, Kelly L. Collins, Devapratim Sarma, Rajesh P. N. Rao, Jeffrey G. Ojemann & Jared D. Olson. "Task-Specific Somatosensory Feedback via Cortical Stimulation in Humans.", *IEEE Transactions on Haptics, DRAFT*. DOI: 10.1109/TOH.2016.2591952.
2. Kay Palopoli-Trojani, Virginia Woods, Chia-Han Chiang, Michael Trumpis & Jonathan Viventi. "In vitro Assessment of Long-Term Reliability of Low-Cost μECoG Arrays.", Micro Electro Mechanical Systems, 2016, IEEE International Conference, 24-28 Jan. 2016, DOI: 10.1109/MEMSYS.2016.7421580.
3. Shota Yamagiwa, Makoto Ishida & Takeshi Kawano. "SELF-CURLING AND—STICKING FLEXIBLE SUBSTRATE FOR ECoG ELECTRODE ARRAY", Micro Electro Mechanical Systems, 2013, IEEE 26th International Conference, 20-24 Jan. 2013. DOI: 10.1109/MEMSYS.2013.647428.

4. Yusuke Morikawa, Shota Yamagiwa, Hirohito Sawahata, Makoto Ishida & Takeshi Kawano. "AN ORIGAMI-INSPIRED ULTRASTRETCHABLE BIOPROBE FILM DEVICE", MEMS 2016, Shanghai, CHINA, 24-28 Jan. 2016, 978-1-5090-1973-1/16/$31.00 ©2016 IEEE, PP. 149-152.
5. Nikita Pak, Joshua H. Siegle, Justin P. Kinney, Daniel J. Denman, Tim Blanche & Ed S. Boyden. Closed-loop, ultraprecise, automated craniotomies. Journal of Neurophysiology 113, April 2015, Pp. 3943-3953.
6. Tian-Ming Fu, Guosong Hong, Tao Zhou, Thomas G Schuhmann, Robert D Viveros & Charles M Lieber., "Stable long-term chronic brain mapping at the single-neuron level.", Nature Methods, Vol. 13, No. 10, October 2016, Pp. 875-882.
7. Chong Xie, Jia Liu, Tian-Ming Fu, Xiaochuan Dai, Wei Zhou & Charles M. Lieber., "Three-dimensional macroporous nanoelectronic networks as minimally invasive brain probes.", Nature Materials, Vol. 14, December 2015, Pp. 1286-1292.
8. Guosong Hong, Tian-Ming Fu, Tao Zhou, Thomas G. Schuhmann, Jinlin Huang, & Charles M. Lieber. "Syringe Injectable Electronics: Precise Targeted Delivery with Quantitative Input/Output Connectivity", Nano Letters, Vol. 15, August 2015, Pp. 6979-6984. DOI: 10.1021/acs.nanolett.5b02987.
9. Jia Liu, Tian-Ming Fu, Zengguang Cheng, Guosong Hong, Tao Zhou, Lihua Jin, Madhavi Duvvuri, Zhe Jiang, Peter Kruskal, Chong Xie, Zhigang Suo, Ying Fang & Charles M. Lieber. "Syringe-injectable electronics", Nature Nanotechnology, Vol. 10, July 2015, Pp. 629-636. DOI: 10.1038/NNANO.2015.115.
10. David T. Bundy, Mrinal Pahwa, Nicholas Szrama & Eric C. Leuthardt., Decoding three-dimensional reaching movements using electrocorticographic signals in humans", Journal of Neural Engineering, Vol. 13, No. 2, 2016, Pp. 1-18. DOI:10.1088/1741-2560/13/2/026021.
11. Takufumi Yanagisawa, Masayuki Hirata, Youichi Saitoh, Haruhiko Kishima, Kojiro Matsushita, Tetsu Goto, Ryohei Fukuma, Hiroshi Yokoi, Yukiyasu Kamitani & Toshiki Yoshimine, "Electrocorticographic Control of a Prosthetic Arm in Paralyzed Patients.", Annals of Neurology, Vol. 71, No. 3, March 2012, Pp. 353-361. DOI: 10.1002/ana.22613.
12. Wei Wang, Jennifer L. Collinger, Alan D. Degenhart, Elizabeth C. Tyler-Kabara, Andrew B. Schwartz, Daniel W. Moran, Douglas J. Weber, Brian Wodlinger, Ramana K. Vinjamuri, Robin C. Ashmore, John W. Kelly & Michael L. Boninger. "An Electrocorticographic Brain Interface in an Individual with Tetraplegia", Plos One, Vol. 8, No. 2, February 2013, Pp. 1-8. DOI:10.1371/journal.pone.0055344.
13. Kay Palopoli-Trojani, Virginia Woods, Chia-Han Chiang, Michael Trumpis & Jonathan Viventi., "In vitro assessment of long-term reliability of low-cost µECoG arrays.", Engineering in Medicine and Biology Society, 38th Annual International Conference of the IEEE, 16-20 Aug. 2016.
14. L. Muller, S. Felix, K. Shah, K. Lee, S. Pannu & E. Chang. "Thin-Film, Ultra High-Density Microelectrocorticographic Decoding of Speech Sounds in Human Superior Temporal Gyrus.", Lawrence Livermore National Laboratory, IEEE Engineering in Medicine and Biology Conference, Orlando, Fla., United States, Aug. 16, 2016 through Aug. 20, 2016. LLNL-CONF-684084.
15. Jonathan Viventi, et al., "Flexible, Foldable, Actively Multiplexed, High-Density Electrode Array for Mapping Brain Activity in vivo.", Nature Neuroscience, Vol. 14, No. 12, Pp. 1599-1605. DOI:10.1038/nn.2973.
16. Thomas J. Oxley et al. Minimally invasive endovascular stent-electrode array for high-fidelity, chronic recordings of cortical neural activity. Nature Biotechnology, Vol. 34, No. 3, February 2016. DOI:10.1038/nbt.3428.
17. Edward S. Boyden, Feng Zhang, Ernst Bamberg, Georg Nagel & Karl Deisseroth, "Millisecond-timescale, genetically targeted optical control of neural activity", Nature Neuroscience, Vol. 8, No. 9, September 2005, Pp. 1263-1268. DOI:10.1038/nn1525.
18. Karl Deisseroth. "Optogenetics", Nature Methods, Vol. 8, No. 1, January 2011, Pp. 26-29. DOI: 10.1038/NMETH.F.324.
19. Karl Deisseroth. "Optogenetics: 10 years of microbial opsins in neuroscience, "Nature Neuroscience, Vol. 18, No. 9, September 2015, Pp. 1213-1225.
20. Andre Berndt Karl Deisseroth." Expanding the optogenetics toolkit: A naturally occurring channel for inhibitory optogenetics is discovered." Science, Vol. 349, No. 6248, Aug. 7, 2015, Pp. 590-591.
21. S. Yamagiwa, M. Ishida & T. Kawano., "Flexible parylene-film optical waveguide arrays.", Applied Physics Letters, Vol. 107, No. 083502, 2015, Pp. 1-5. DOI: 10.1063/1.4929402.
22. Michael Joshua Frank, Johan Samanta, Ahmed A. Moustafa & Scott J. Sherman. "Hold Your Horses: Impulsivity, Deep Brain Stimulation, and Medication in Parkinsonism.", Science, Vol 318, No. 5854, December 2007, Pp. 1309-1312. DOI: 10.1126/science.1146157.
23. David J. Foster & Matthew A. Wilson. "Reverse replay of behavioural sequences in hippocampal place cells during the awake state.", Nature 04587, Pp. 1-4. DOI: 10.1038.
24. Nir Grossman, David Bono, Nina Dedic, Suhasa B. Kodandaramalah, Andrii Rudenko, Ho-Jun Suk, Antonino M. Cassara, Esra Neufeld, Niels, Li Huei Tsai, Alvaro Pascual-Leone and Edwards S. Boyden, "Non-Invasive Deep Brain Stimulation via Temporally Interfering Electric Fields", Cell 169, pp 1029-1041, Jun. 1, 2017.
25. U.S. Pat. No. 8,121,694 to Molnar et al. entitled "Therapy control based on a patient movement state".
26. Oxley et al., "Minimally invasive endovascular stent-electrode array for high-fidelity, chronic recordings of cortical neural activity", in Nature Biotechnology 34(3), February 2016 DOI: 10.1038/nbt.3428.
27. Emiliany et al "All-Optical Interrogation of Neural Circuits" in The Journal of Neuroscience, Oct. 14, 2015-35(41):13917-13926.

The type of electrical activity which may be sensed/recorded by the sensing/stimulating electrode set(s) 12 may include single neuron electrical activity (extracellularly recorded single neuronal action potentials), simultaneously sensed/recorded electrical activity of several neurons (extracellularly recorded multiple neuronal action potentials), sensed extracellularly recorded field potentials, Electrocorticogram type sensing/recording (Ecog) of summed electrical activity from multiple neurons (such as, Ecog recorded with surface recording Ecog array types).

Additionally, while electrode sets including electrically conducting electrodes for recording neuronal electrical activities representative of single or multiple neuronal electrical activities and for electrically stimulating single or multiple neurons are preferred due to their well characterized properties and interactions with neuronal tissues, the systems of the present application are not limited to electrically recording and stimulation types of devices using such electrode sets. Rather, other types of sensing and/or stimulating devices may also be used to replace the electrode set(s) 12 of the system 10. For example, sensing and/or stimulating devices using optical detection of neuronal tissue activity may be used and possibly stimulating devices using optical methods for stimulating single or multiple neurons may also be used. Such optical devices are disclosed for example in the following references:

1. Edward S. Boyden, Feng Zhang, Ernst Bamberg, Georg Nagel & Karl Deisseroth., "Millisecond-timescale, genetically targeted optical control of neural activity.", Nature Neuroscience, Vol. 8, No. 9, September 2005, Pp. 1263-1268. DOI:10.1038/nn1525.
2. Karl Deisseroth. "Optogenetics.", Nature Methods, Vol. 8, No. 1, January 2011, Pp. 26-29. DOI: 10.1038/NMETH.F.324.
3. Karl Deisseroth. "Optogenetics: 10 years of microbial opsins in neuroscience, "Nature Neuroscience, Vol. 18, No. 9, September 2015, Pp. 1213-1225.
4. Andre Berndt, and Karl Deisseroth." Expanding the optogenetics toolkit: A naturally occurring channel for inhibitory optogenetics is discovered." Science, Vol. 349, No. 6248, Aug. 7, 2015, Pp. 590-591.

Other types of electrode sets that may be usable in the systems of the present application may include any type of electrode sets(s) disclosed in any references disclosed in the present application.

For example theoretical calculations indicate that certain types of "neural dust" implementations using ultrasonic communication methods may enable very small (about 50 micron sized) non-tethered wireless devices to be implanted in neuronal tissues for sensing and/or stimulation purposes. Examples of such neural dust implementations may be found in the following publications:

1. Dongjin Seo, Ryan M. Neely, Konlin Shen, Utkarsh Singhal, Elad Alon, Jan M. Rabaey, Jose M. Carmena and Michel M. Maharbiz, entitled "Wireless Recording in the Peripheral Nervous System with Ultrasonic Neural Dust", published in Neuron 91, 529-539, Aug. 3, 2016.
2. Biederman William et al. "A Fully Integrated Miniaturized (0.125 mm2) 10.5 μW wireless neural sensor". Published in IEEE Journal of solid State Circuits, Vol. 48 Issue 4, April 2013: DOI: 10.11o9/JSSC 2013.2238994.

Ecog electrode arrays, methods for their use and methods and algorithms for analyzing neuronal activity related signals sensed thereby are disclosed, among others, in the following publications:

1. David T Bundy, Mrinal Pahwa, Nicolas Szrama and Eric C Leuthardt, "decoding three-dimensional reaching movements using electrocorticographic signals in humans", J. Neural Eng. 13, 23 Feb. 2016.
2. Gerwin Schalk and Eric C Leuthardt, "Brain-Computer Interfaces Using Electrocorticographic signals", IEEE Reviews In Medical Engineering, Vol. 4, 2011.
3. Eric C Leuthardt, Gerwin Schalk, Jonathan R Wolpaw, Jefrey G Ojemann and Daniel W Moran; "A Brain-Computer Interface Using Electrocorticographic Signals In Humans". J. Neural Eng. 1. Pp. 63-71 (2004).

The sensing/stimulating electrode set(s) 12 may be any combination of one or more electrodes or electrode sets of several types. For example, for cortical region sensing/stimulation, the electrode set(s) 12 may include surface recording semi-invasive electrodes with single or multiple electrodes placed on the surface of the brain, invasive electrode set(s), such as one or several Utah arrays or other multi-electrode array types that are invasively implanted within the relevant cortical layers by penetrating the cortical surface. Invasively implanted Ecog type electrode arrays disposed on a cortical surface or on the surface of the Dura.

In operation, the system 10 may stimulate one or more regions of the visual cortex in a spatio-temporal pattern of stimulation that results in the user perceiving a virtual image in his/her FOV. The term "virtual image" is used here to indicate that the image is induced solely by stimulating the visual cortex or a part or parts thereof and is not the result of any visual stimulation of the user's eyes.

The virtual image may be or may include a virtual GUI. It is noted that as the user may be normally using his visual system, the virtual image or the virtual GUI may be experienced by the user as overlying or superimposed on or beneath the image representing the environment that the user is visually observing with his eye/brain system.

In a non-limiting example, the stimulation of the visual cortex by the stimulating electrodes of the sensing/stimulation electrode set 12 may result in a perceived image of two spatially separate regions in the FOV of the user, for example a red circle and a separate blue circle. When the user imagines moving his arm to overlap the red circle, the system may decode the sensed cortical electrical signals, compute the direction and amplitude of the imagined movement and may interpret this input as a "NO" instruction to the program. When the user imagines moving his arm to overlap the blue circle, the system may decode the sensed cortical electrical signals, compute the direction and amplitude of the imagined movement and may interpret this input as a "YES" instruction to the program. Various other types of virtual images evoked by cortical stimulation may be used as virtual GUIs, as is disclosed in detail hereinafter with respect to FIGS. 7-12.

It is noted that methods of processing electrical signals recorded in the pre-motor and/or motor cortex of patient for interpreting and detecting the patient's intended movement are well known in the art, are not by themselves the subject matter of the present invention and are therefore not described in detail hereinafter. Any suitable methods for processing/decoding electrical signals recorded from the motor and/or pre-motor cortical regions and using the results of the processing/decoding for providing output usable for controlling a computer software program may be used in the systems and methods of the present application.

For example, the following references disclose methods for processing/decoding motor or pre-motor cortical signals:

1. David T Bundy, Mrinal Pahwa, Nicholas Szrama and Eric C. Leuthardt "decoding three-dimensional reaching movements using electrocorticographic signals in humans" J. Neural Eng. 13 (2016) 026021 (18pp) doi: 10.1088/1741-2560/13/2/026021.
2. Jennifer L Collinger, Brian Wodlinger, John E Downey, Wei Wang, Elizabeth C Tyler-Kabara, Douglas J Weber, Angus J C McMorland, Meel Velliste, Michael L Boninger, Andrew B Schwartz "High-performance neuroprosthetic control by an individual with tetraplegia" Lancet 2013; 381: 557-64.
3. Leigh R. Hochberg, Mijail D. Serruya, Gerhard M. Friehs, Jon A. Mukand, Maryam Saleh, Abraham H. Caplan, Almut Branner, David Chen, Richard D. Penn and John P. Donogh, "Neuronal ensemble control of prosthetic devices by a human with tetraplegia" Nature, Vol 442|13 Jul. 2006|doi:10.1038/nature04970.
4. P. R. Kennedy, R. A. E. Bakay, M. M. Moore, K. Adams, and J. Goldwaithe "Direct Control of a Computer from the Human Central Nervous System", IEEE TRANSACTIONS ON REHABILITATION ENGINEERING, VOL. 8, NO. 2, pp. 198-202, June 2000.

5. Moran D W, Schwartz A B. Motor cortical representation of speed and direction during reaching. J. Neurophys. 1999; 82:2676-2692.
6. Andrew B. Schwartqa Ronald E. Kettner, b and Apostolos P. Georgopoulos, "Primate Motor Cortex and Free Arm Movements to Visual Targets inThree-Dimensional Space. I. Relations Between Single CellDischarge and Direction of Movement" The Journal of Neuroscience, August 1988, B (8): 2913-2927.
7. Dawn M. Taylor, Stephen I. Helms Tillery, Andrew B. Schwartz. "Direct Cortical Control of 3D Neuroprosthetic Devices" Science, Vol 296 pp. 1829-1832, 7 Jun. 2002.
8. B Wodlinger, J E Downey, E C Tyler-Kabara, A B Schwatz, M L Boninger and J L Collinger, "Ten-dimensional anthropomorphic arm control in a human brain— machine interface: difficulties, solutions, and limitations" J. Neural Eng. 12 (2015) 016011 (17pp) doi:10.1088/1741-2560/12/1/016011.

It is noted that while the sensing/stimulating electrode set(s) 12 of the system 10 may be implemented as a single electrode array that is placed in contact with both the motor/pre-motor cortical region(s) and the visual cortical region(s) such that some of the electrodes in the sensing/stimulating electrode set(s) 12 may stimulate visual cortical region(s) and other electrodes in the sensing/stimulating electrode set(s) 12 may sense/record signals from motor and/or pre-motor cortical region(s), this is not obligatory and in some embodiments, the stimulating and sensing may be performed by two different electrode sets.

Figure 2:
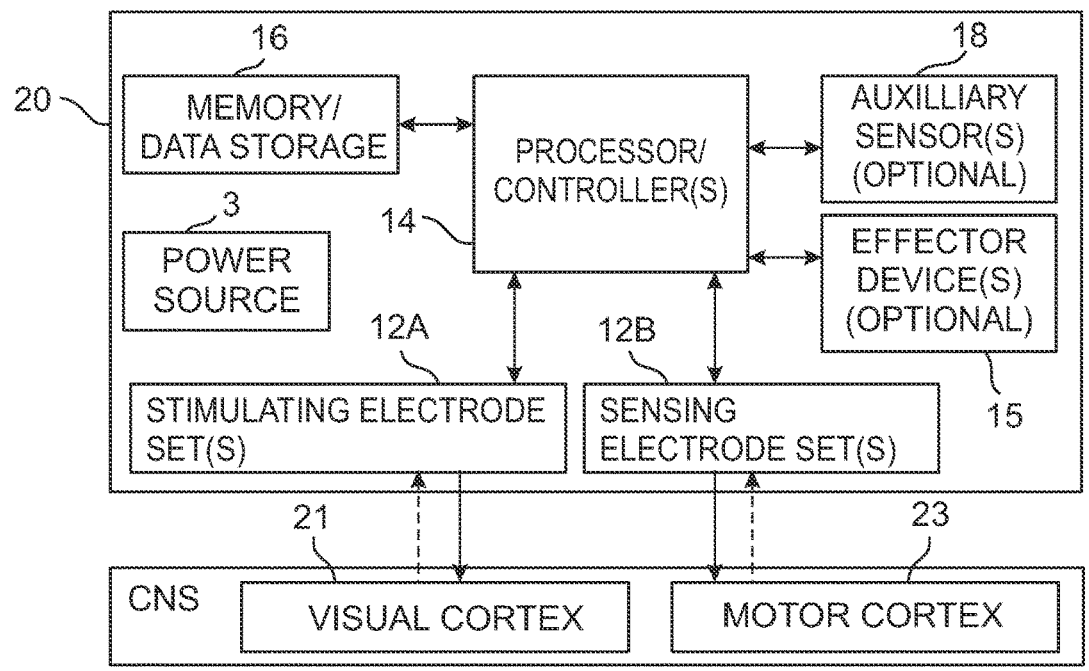
FIG. 2 is a schematic block diagram, the components of a general user interface system usable for performing general computing tasks, in accordance with an embodiment of the systems of the present application.

Reference is now made to FIG. 2 which is a schematic block diagram, illustrating the components of a general user interface system usable for performing general computing tasks having two different electrode sets, in accordance with some embodiments of the systems of the present application. The system 20 includes the processor controller(s) 14 as disclosed in detail hereinabove. The system 20 may also include the memory/data storage device(s) 16, the (optional) auxiliary sensor(s) 18 and the (optional) effector device(s) 15 suitably coupled to the processor/controller(s) 14 as disclosed in detail hereinabove. The effector device(s) 15 may be any of the effector devices described hereinabove with respect to FIG. 1. The system 20 may also include a sensing electrode set 12B for sensing (and/or recording) neuronal activity in the motor cortex 23 (and/or optionally in the pre-motor cortex) and another sensing electrode set 12B for stimulating the primary visual cortex 21 (and/or, in some embodiments, any other parts of the visual cortex) for causing the user of the system 20 to perceive a virtual image within the field of view of the user as a result of the stimulation of the visual cortex by the stimulating electrode set 12A.

The virtual image may be integrated with or superimposed over the "real" visual image of the environment as received by the eyes of the user and relayed normally through the visual pathway to the visual cortex.

The virtual image perceived by the user of the system 20 may be any desired image usable by the user for performing various tasks and/or for presenting data or information to the user (such as internal bodily information or provided by any medical sensors included the auxiliary sensor(s) 18).

The information or data presented to the user may be graphic information (an image or images), and/or alphanumeric (such as textual information including characters and/or numbers) and any suitable combination of such visually perceptible images. For example, by stimulating the primary visual cortex 21 (and/or any other part or region of the visual cortex) a virtual image may be perceived by the user, which virtual image may be or may include a GUI which may enable the user to perform one or more general computing task. Such general computing tasks may include but are not limited to, operating and/or controlling the operation of any software program(s) (or any subroutine thereof) which is operable on the processor/controller(s) 14.

Figure 3:
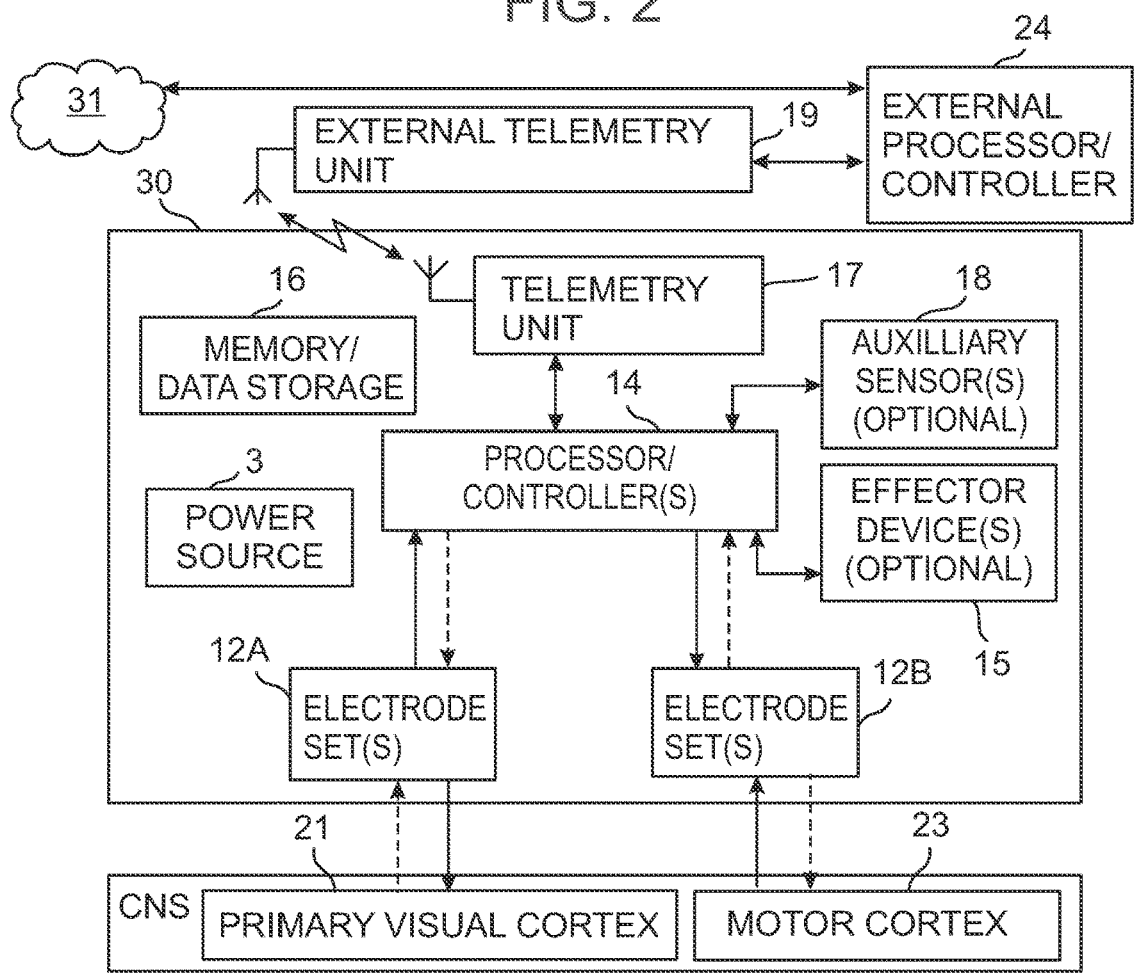
FIG. 3 is a schematic block diagram illustrating an embodiment of a general user interface system usable for performing general computing tasks and having wireless communication capabilities, in accordance with some embodiments of the systems of the present application.

Such programs may, for example, enable the user to control the operation of any of the auxiliary sensor(s) 18 and/or the effector devices 15 disclosed in reference to FIGS. 1-3. However, The systems for presenting and interacting with a virtual GUI disclosed in the present application may be used to interact with and/or control the operation of any other type of program or operating system operating on the processor/controller(s) 14 (of FIGS. 1-3), the processor/controller(s) 124 (of FIG. 4), and/or the external processor controller 24 (of FIG. 3) and/or the external processing/programming unit(s) 179 of FIGS. 4-5 (including but not limited to the computer 181 and the mobile phone 183 of FIG. 6), and/or operating on any other type of controller, and/or processor, and/or microprocessor and/or computer and/or server, and/or mainframe wirelessly linked to systems disclosed herein through any type of communication network (including any LAN, WAN, the internet, a VPN or any other type of network known in the art. Such programs controllable by the user may also include programs operating on any processor included in one or more of the auxiliary sensor unit(s) 18 and/or in one or more of the effector device(s) 15 disclosed herein.

For example, the stimulating of the primary visual cortex 21 may cause the user to perceive a virtual dialog box superimposed upon the normally perceived field of view (FOV) visibly observed by the user. Such virtual dialog box may include selectable options that may be selected or chosen by "pointing at" or "clicking" on "virtual buttons" included in the virtual dialog box by, for example moving a virtual cursor over to the virtual button.

Additional embodiments may include the ability to move more virtual limbs by moving or planning to move or imagining the moving of one physical limb. In traditional virtual reality (VR) devices and systems, such interactive images for controlling computing tasks are typically presented to the user by a HUD device or by virtual reality goggles or eyeglasses and are projected into the retina of the user to be conveyed normally through the visual pathway of the user to be perceived by the user. However, in contrast, the virtual image(s) and virtual GUI of the present application are a result of direct stimulation of the visual cortex (primary visual cortex and/or any other region(s) of the visual cortex or any desired combination of such regions of the visual cortex).

A paper by WM. H Dobelle, entitled "Artificial Vision for the Blind by Connecting a Television Camera to the Visual Cortex" published in *ASAIO Journal* 2000 discloses systems for presentation of images acquired by using an imaging device (such as a video camera mounted on the user's body), translating the image to a pattern of electrical stimulating signals that are delivered by an electrode array having multiple electrodes to the visual cortex for direct stimulation of the visual cortex. The system has been successfully used for providing blind patients with an image (composed of phosphene type perceived images) roughly representing the environment as sensed by the video camera. Other articles disclosing methods and devices usable in the system may include:
1. Dobelle W H, Mladejovsky M G: Phosphenes produced by electrical stimulation of human occipital cortex, and their application to the development of a prosthesis for the blind. *J Physiol (Lond)* 243: 553-576, 1974.
2. Dobelle W H, Mladejovsky M G, Girvin J P: Artificial vision for the blind: Electrical stimulation of visual cortex offers hope for a functional prosthesis. Science 183: 440-444, 1974.
3. Dobelle W H, Mladejovsky M G, Evans J R, Roberts T S, Girvin J P: "Braille" reading by a blind volunteer by visual cortex stimulation. Nature 259: 111-112, 1976.
4. Dobelle W H, Quest D, Antunes J, Roberts T, Girvin J P: Artificial vision for the blind by electrical stimulation of the visual cortex. Neurosurgery5: 521-527, 1979.
5. Klomp G F, Womack M V B, Dobelle W H: Fabrication of large arrays of cortical electrodes for use in man. J Biomed Mater Res 11: 347-364, 1977.

The above references describe systems used to enable a blind person to perceive a representation of his visual environment by using an imaging device (a video camera) to form an image of parts of the surrounding environment, transforming the resulting image into stimulating signals for visual cortical stimulation and delivering the cortical stimulation to present to the blind person an image representative of the surrounding environment. However, such systems do not teach or even fairly suggest any means of interaction of the user with the perceived image nor did they teach or even fairly suggest the use of the presented image as a GUI.

However, in the systems disclosed in the present application (such as, for example the systems 10 and 20) the user may interact with the virtual image (such as the virtual dialog box, a cursor image, or any other graphic image or symbol) by using the sensing electrodes (such as, but not limited to, the sensing electrode set(s) 12B) to sense neuronal activity in the motor cortex 23 resulting from the user voluntarily moving an arm or even actively planning or intending or imagining to move an arm (without actually moving the arm) in a certain direction.

It is also noted that the use of BCIs to sense neuronal activity in the motor cortex to control the movement of a prosthesis is well known in the art and may be performed by suitable processing of the signals sensed in the motor cortex to generated commands for operating the prosthesis as is disclosed in detail by David T. Bundy, Mrinal Pahwa, Nicholas Szrama & Eric C. Leuthardt, in the paper entitled, "Decoding three-dimensional reaching movements using electrocorticographic signals in humans.", published in *Journal of Neural Engineering*, Vol. 13, No. 2, 2016, Pp. 1-18. DOI:10.1088/1741-2560/13/2/026021.

To the best knowledge of the inventor of the present invention, using the sensing and processing of neuronal activity in the motor cortex to interact with a virtual image presented to the user by direct stimulation of the visual cortex for the purpose of performing a general computing task has never been taught or even fairly suggested.

The general computing tasks that may be performed by the user using the virtual GUI to interact and control a software program, may be, for example, initiating, or starting or stopping the execution of a computer program programmed into the processor/controller(s) 14, interacting with a virtual graphic user interface of such a program (presented by stimulation of the visual cortex by the stimulating electrode set(s) 12A under control of the processor/controller(s) 14), displaying data and/or information to the user, interacting with a virtual GUI for controlling the operation of one or more of the effector device(s) 15 through a computer software residing in the processor/controller 14, or any other type of computing task performable by such voluntary active interaction through sensing of the electrical signals in the motor cortex (and/or pre-motor cortex) and processing the sensed signals to control the interaction of the user with a virtual image perceived as a result of stimulation of the visual cortex of the user (the stimulation being controlled by the processor/controller(s) 14).

One of the advantages of the systems disclosed in the present application is that it eliminates the need for an HUD or VR goggles or other VR devices, since the virtual image is perceived by the user as a result of directly stimulating the visual cortex.

Another advantage is that, in contrast to performing real limb movements to interact with an image, recording in the pre-motor and/or motor cortex may be faster as it may precede the activity in the motor cortex and musculo-skeletal system activation by a substantial amount of time (typically by about 200-500 microseconds). Thus, the systems disclosed herein may advantageously react faster than other systems using VR equipment to performing tasks, which may improve the user reaction time in certain tasks. For example, this may be highly advantageous for improving the speed of operating and/or controlling of certain types of the effector device(s) 15. In such tasks as, for example, operation of an airborne vehicle, or a land vehicle, where reaction time of the user may be very important, there is a clear advantage to the systems disclosed herein. Another advantage may be the ability to control several virtual limbs from the movement planning, or direct movement of a single limb. This one-to-many approach may allow users finer or more multi-dimensional control, in a very intuitive manner.

Reference is now made to FIG. 3 which is a schematic block diagram illustrating an embodiment of a general user interface system usable for performing general computing tasks and having wireless communication capabilities, in accordance with some embodiments of the present application. The system 30 is similar to the system 20, except that that in addition to the processor/controller 14 the memory/data storage 16, the stimulating electrode set 12A, the sensing electrode set 12B, the power source 3, the (optional) auxiliary sensor(s) 18 and the (optional) effector device(s) 15, which are connected and operative as disclosed in detail for the system 20, the system 30 also includes a telemetry unit 17, suitably connected to the processor/controller 14. The effector device(s) 15 may be any of the effector devices described hereinabove with respect to FIG. 1.

The telemetry unit 17 may be used for wirelessly and bidirectionally communicating with an external telemetry unit 19. The external telemetry unit 19 may be suitably connected to an external processor/controller unit 24. The telemetry unit 17 may bidirectionally communicate with the processor/controller(s) 14 and may be used to wirelessly communicate data from the memory/data storage 16 and/or from the processor/controller(s) 14 through the external telemetry unit 19 to the external processor/controller 24 for further processing, further storage and for displaying the data. In some embodiments of the system, the external processor/controller 24 may use the external telemetry unit 19 to wirelessly send signals to the processor/controller(s) 14 for controlling the operations thereof and/or for reprogramming the software operating the controller processor(s) 14. For example, when some or all of the processor/controllers(s) 14, the electrode sets 12A, 12B and 12C, the memory/storage 16, the auxiliary sensor(s) 18 and the effector device(s) 15 are implanted intra-cranially, the telemetry unit 17 may be intra-cranially disposed for wireless communication with an external telemetry unit 19 as disclosed hereinabove.

It is noted that while the external telemetry unit 19 and the external processor controller 24 are shown as separate units, this is not obligatory and in some embodiments of the system 30, they may be integrated into one device. For example, in accordance with some embodiments any laptop, desktop, tablet, pablet, cellular telephone, smartphone or hand held device that has a processor unit and wireless communication capability may be used for communicating with the internal telemetry unit 17 (for example by using WiFi or any other suitable communication protocol/device). In some embodiments, such devices may also be suitably connected to the cloud 31 through the internet to enable the off loading of data for storage and/or for using the cloud for processing the recorded data.

The following publications disclose, inter alia, disclose methods and devices for performing stimulation and/or recording of brain structures are disclosed in detail in the following publications incorporated herein by reference in their entirety:

1. Jesse J. Wheeler, Keith Baldwin, Alex Kindle, Daniel Guyon, Brian Nugent, Carlos Segura, John Rodriguez, Andrew Czarnecki, Hailey J. Dispirito, John Lachapelle, Philip D. Parks, James Moran, Alik S Widge, Darin D. Dougherty & Emad N. Eskandar. "An implantable 64-channel neural interface with reconfigurable recording and stimulation.", *IEEE Xplore Digital Library*, www(dot)ieeexplore(dot)ieee(dot)org/document/7320208.
2. Lei Hamilton, Marc McConley, Kai Angemueller, David Goldberg, Massimiliano Corba, Louis Kim, James Moran, Philip D. Parks, Sang Chin, Alik S Widge, Darin D. Dougherty & Emad N. Eskandar. "Neural signal processing and closed-loop control algorithm design for an implanted neural recording and stimulation system.", *IEEE Xplore Digital Library*, www(dot)ieeexplore(dot)ieee(dot)org/document/7320207.
3. Beata Jarosiewicz, Anish A. Sarma, Daniel Bacher, Nicolas Y. Masse, John D. Simeral, Brittany Sorice, Erin M. Oakley, Christine Blabe, Chethan Pandarinath, Vikash Gilja, Sydney S. Cash, Emad N. Eskandar, Gerhard Friehs, Jaimie M. Henderson, Krishna V. Shenoy, John P. Donoghue & Leigh R. Hochberg. "Virtual typing by people with tetraplegia using a self-calibrating intracortical brain-computer interface." Science Translational Medicine, American Association for the Advancement of Science, Vol. 7, Issue 313, 11 Nov. 2015.

Methods and devices for sensing electrical cortical activity in various cortical regions and for stimulating cortical regions are disclosed in detail in references cited in the present application, but are not limited to the references cited hereinabove. Any of these methods and electrode set(s) and devices known in the art and described in the references cited herein may be used for sensing/recording neuronal activities in the motor and/or pre-motor cortex and for stimulating the visual cortex. For example, the injectable flexible mesh electrodes such as the one disclosed by Tian Ming Fu et al. (Nature methods, 2016) may be used by implantation of such mesh electronics within the relevant cortical regions. Another method may use the less invasive flat flexible surface electrode arrays (such as those described by Dobelle in the references disclosed herein. Other systems and methods may make use of stent electrode arrays (stentrodes) as disclosed hereinabove.

Figure 4:
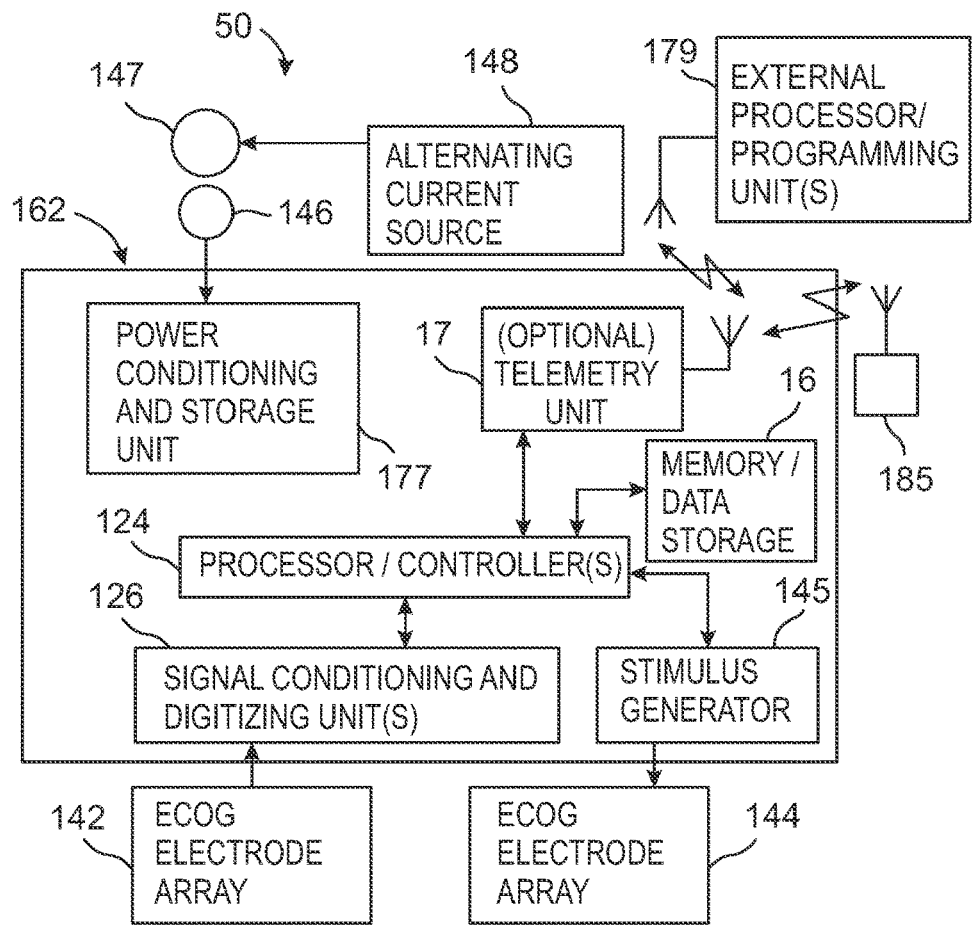
FIG. 4 is a schematic block diagram illustrating an implanted virtual user interface system, disposed within the cranium of the user and using Ecog electrode arrays, in accordance with some embodiments of the systems of the present application.
Figure 5:
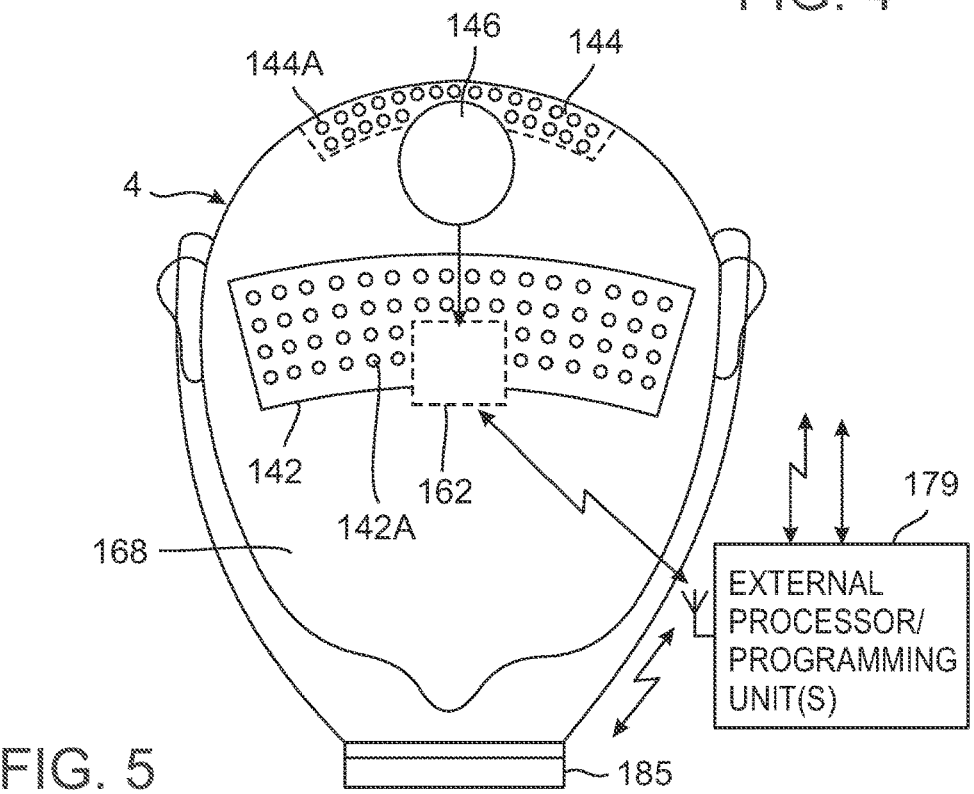
FIG. 5 is a schematic top view illustrating the positions of some of the components of the system of FIG. 4 in relation to a user's head.
Figure 6:
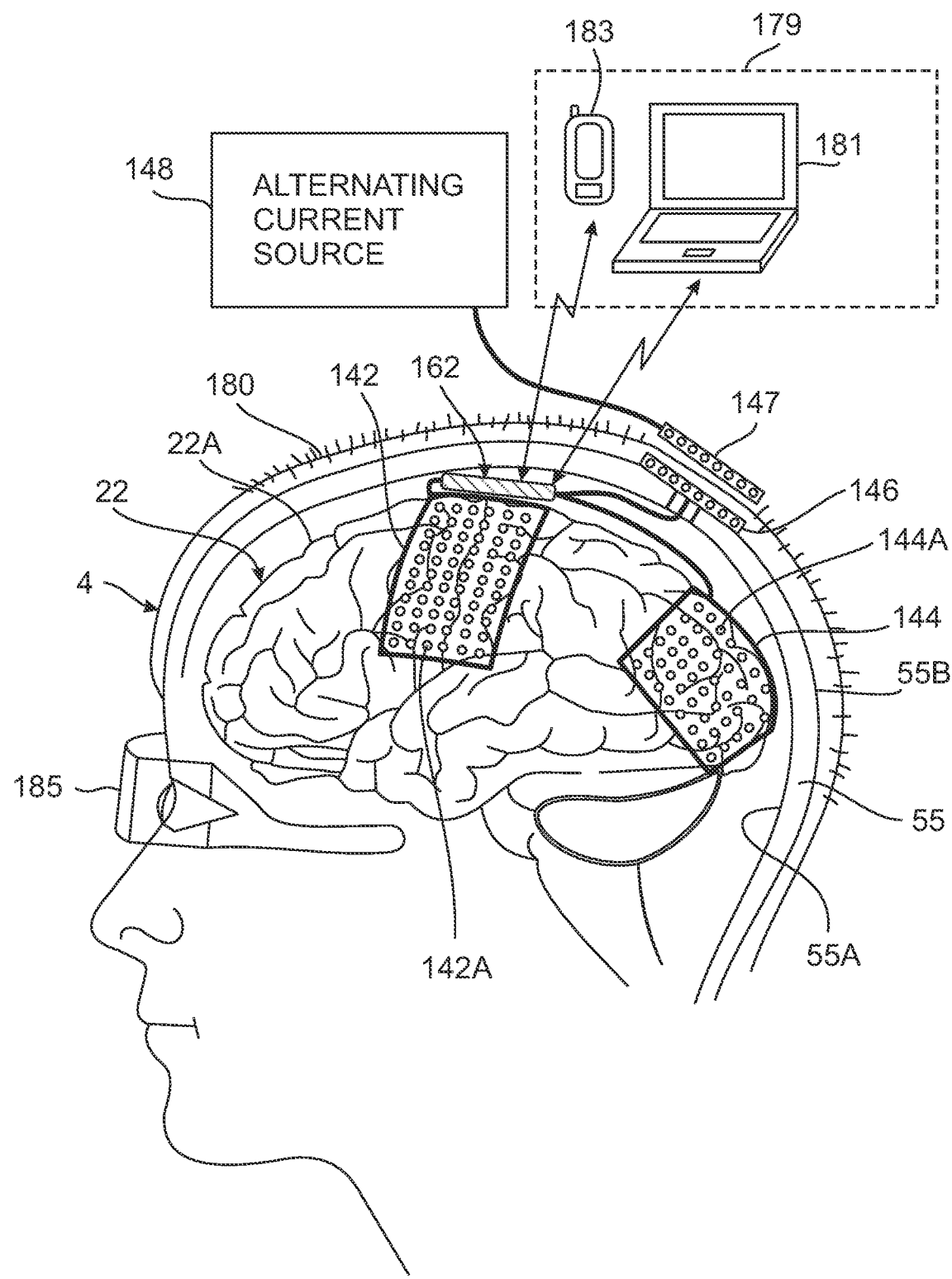
FIG. 6 is a schematic part cross-sectional part side view illustrating the positioning of some of the components of the system of FIG. 4 in relation to a user's head.

Reference is now made to FIGS. 4-6. FIG. 4 is a schematic block diagram illustrating an implanted virtual user interface system, disposed within the cranium of the user and using Ecog electrode arrays, in accordance with some embodiments of the systems of the present application. FIG. 5 is a schematic top view illustrating the positions of some of the components of the system of FIG. 4 in relation to a user's head. FIG. 6 is a schematic part cross-sectional part side view illustrating the positioning of some of the components of the system of FIG. 4 in relation to a user's head.

Turning now to FIGS. 4-5, the system 50 may include an implantable electronics module 162, two ECOG electrode arrays 142 and 144 suitably electrically connected to the electronics module 162, and an implantable induction coil 146 suitably electrically connected to the electronics module 162. The implantable induction coil 146 may be used for wirelessly harvesting electrical power from an external induction coil 147 that is suitably electrically connected to an alternating current source 148. The implantable electronics circuitry module 162 includes one or more processor/controller(s) 124, a power conditioning and storage unit 177, electrically coupled to an induction coil 146, a telemetry unit 17 suitably electrically coupled to the processor/controller(s) 124, a memory/data storage unit 16 suitably electrically connected to the processor/controller(s) 124 and a signal conditioning and digitizing unit(s) 126 electrically connected to the ECOG array 142 to receive sensed signals from the electrodes of the ECOG arrays 142. The conditioning and digitizing unit(s) 126 is also connected to the processor/controller(s) 124 for sending digitized sensed ECOG signal's data to the processor/controller(s) 126 for further processing.

The electronic circuitry module may also include a stimulus generator 145 that is suitably electrically coupled to the electrodes of the ECOG array 144. The stimulus generator is suitably electrically connected to the processor/controller(s) 124 for receiving control signals therefrom to control the electrical stimulation of the visual cortical regions by the ECOG array 144. The stimulus generator 145 may stimulate the visual cortical region(s) by passing stimulating current signals through any of the individual electrodes 144A of the ECOG array 144 (or through pares of the electrodes 144A.

The system 50 may include one or more external processor/programming unit(s) 179. The telemetry unit 17 may bidirectionally wirelessly communicate with the external processor/programming unit(s) 179, enabling bidirectional wireless transfer of data, control signals and status signals between the processor/controller 124 and the processor/programming unit(s) 179. For example, in accordance with some embodiments, the external processor/programming unit may be implemented as any laptop, desktop, tablet, pablet, cellular telephone, smartphone or hand held device that has a processor unit and wireless communication capability for communicating with the internal telemetry unit 17 (for example, by using WiFi or any other suitable communication protocol/device). In some embodiments, such devices may also be suitably connected (using a wired or wireless connecting method) to the cloud 31 (not shown in FIG. 4 for the sake of clarity of illustration, but see FIG. 5) through the internet to enable the off loading of data for storage and/or for using the cloud for processing the recorded data.

The electronics module 162 also includes a power conditioning and storage unit 177. It is noted that the power conditioning and storage unit 177 may be connected to an induction coil 146 that may be implanted under the scalp 180 of the patient (FIG. 6). The induction coil 146 is suitably electrically connected to the power conditioning and storage unit 177. To provide power to the system 50, a second induction coil 147 may be placed on the surface of the scalp 180 adjacent to the implanted induction coil 146. The second induction coil 148 may be suitably electrically connected to an alternating current source 148. Alternating currents passing within the second induction coil 147 induce alternating currents within the implanted induction coil 146. The alternating currents flowing within the induction coil 146 may be rectified by suitable current rectifying diode bridge circuitry (not shown) included in the power conditioning and storage unit 177 and charge may be stored by any suitable charge storage device (not shown) such as, for example, a supercapacitor, a capacitor, or a rechargeable electrochemical cell included within the power conditioning and storage unit 177. The power conditioning and storage unit 177 is used for energizing any of the current requiring electrical components of the electronic circuitry module 152. It is noted that the electrical connections supplying electrical power to the components of the electronic circuitry module 152 are not shown in FIGS. 4-6 for the sake of clarity of illustration.

The system 50 may also (optionally) include an AR headset 185. The AR headset 185 is a wireless device that may include a power source (such as, for example, a battery, rechargeable battery or any other suitable power source) and a telemetry unit (not shown in detail) that may operate to enable wireless communication with the controller/processor(s) 124 of the electronic circuitry module 162. The AR headset 185 may also be wirelessly in communication with the external processor/programming unit(s) 179 (of FIG. 4) and/or with laptop 181 and/or with the mobile phone 183 (of FIG. 6 hereinafter).

It is noted that the AR headset 185 may be connected to the cloud 31 that may be accessible to the external processor/programming unit(s) 179 in a wired or wireless manner. This may be useful for offloading some of the computational load from the processor/controller(s) 124 and/or from the external processor/programming unit(s) 179 and/or from any processing unit (not shown in detail) included in the AR headset 185. In such an arrangement, at least some processing tasks of parts of the system 50 (such as, for example rendering tasks and/or other computationally intensive tasks performed) may be performed on a cloud CPU and/or cloud GPU located in a remote server or computing processor cluster.

Turning to FIG. 6, the ECOG array 142 may be surgically intra-cranially implanted and placed on the surface of the motor and/or pre-motor cortical regions (or part(s) thereof) and the ECOG array 144 may be surgically intra-cranially implanted and placed on the surface of the visual cortical regions (or part(s) thereof) using standard surgical procedures. The ECOG array 142 has multiple electrodes 142A that may be used for sensing electrical activity in the motor and/or pre-motor regions of the cortex 22. The ECOG array 144 has multiple electrodes 144A that may be used for electrically stimulating one or more parts of the visual regions of the cortex 22.

The electronic circuitry module 162 may be implanted intra-cranially in the space between the inner surface 55A of the calvarial bone 55 and the surface 22A of the cortex 22. Alternatively, in some embodiments, the electronic circuitry module 162 may be implanted within the calvarial bone 55, such as, for example between the inner table and the outer table of the calvarial bone (not shown in FIG. 6) or in some other embodiments between outer table of the calvarial bone 55 and the scalp 180 of the user's head 4.

The induction coil 146 (connected to the electronic circuitry module 162) may be implanted between the outer surface 55B of the calvarial bone 55 and the scalp 180. Alternatively, in some embodiments, the induction coil 146 may be implanted within the calvarial bone 55, or even in the space between the surface 22A of the cortex 22 and the inner surface 55A of the calvarial bone 55.

In operation of the system 50, the ECOG array 144 may be used to electrically stimulate the visual cortical areas or parts thereof to present to the user or patient one or more virtual images. The virtual image(s) may be superimposed on or co-perceived with the normal visual image of the user's environment within the FOV of the user that results from the light stimulation of the retinas of the eyes and processed by the visual pathways system of the user (through the LGN and other processing CNS regions of the visual system. The virtual image may then be used by the user as a virtual GUI for interacting with and controlling the operation a software program that may be operating on the processor/controller(s) 124 and/or on the external processor/programming unit 179 and/or on any other processor/controller in wired or wireless communication with the processor/controller(s) 124 and/or on the external processor/programming unit 179 (such as, for example, a server operative in the world wide web).

Returning to FIG. 6, the telemetry unit 17 of the electronic circuitry module 162 may wirelessly communicate with the external processing/programming unit(s) 179 which in the specific (non-limiting) embodiment illustrated in FIG. 6 includes a laptop computer 181 and/or a mobile phone 183. In some embodiments, the telemetry unit 17 may have a dedicated antenna (not shown in FIG. 6 for the sake of clarity of illustration) suitably included in or connected to the electronic circuitry module 162. Such an antenna may be disposed intra-cranially, or may be disposed within the calvarial bone (preferably, in the cancellous bone layer of the calvarial bone. Alternatively, in some embodiments, the antenna may be disposed between the outer surface 55B of the calvarial bone and the scalp 180.

In some embodiments, the induction coil 146 may be used as an antenna by suitably connecting it to the telemetry unit 17 of the electronic circuitry module 162.

The user's interaction with the virtual GUI may be performed as disclosed in detail hereinabove and hereinafter (with reference to FIGS. 7-12). The interaction may be performed by the user either moving a limb or few limbs (such as, for example a hand or two hands) or intending to move the limb(s) or imagining the moving of the limb(s). Such moving or intending to move or imagining performing the movement may result in electrical activity in the relevant parts of the pre-motor and/or motor cortex. The ECOG array 144 may sense the electrical signals in the motor and/or pre-motor cortex. The sensed signals may be conditioned (amplified and/or filtered) and digitized by the signal conditioning and digitizing unit(s) 126 of the electronic circuitry module 162, and the digitized signals may be fed to the processor/controller(s) 124 for processing and decoding (according to any of the processing methods disclosed in the present application.

The electrical signals sensed/recorded in the pre-motor and/or motor cortex may then be processed by the processor/controller(s) 124 and/or on the external processor/programming unit 179 to decode the parameters of the user's movement or the intended or imagined movement. For example the decoding may compute the amplitude and direction of the movement (performed or imagined or intended). The decoded movement parameters may then be used to detect the position of the movement's target relative to the virtual GUI image and use this position to interact with or control the operation of a program performing a general computing task (or any other computer assisted or computer controlled task by producing proper control signals to the relevant software.

In accordance with a non-limiting example, if the virtual GUY perceived by the user includes two different image parts on the left and right sides of the visual field of the user (one representing a "YES" decision and the other representing a "NO" decision) if the decoding of the limb movement or the imagined movement result in movement parameter values indicating that the movements target was within (or near) the "NO" representing image part of the virtual GUI, the software may interpret this as a NO decision made by the user. Conversely, if the decoding of the limb movement or the imagined movement result in movement parameter values indicating that the movements target was within (or near) the "YES" representing image part of the virtual GUI, the software may interpret this as a "YES" decision made by the user. Thus, by performing limb movement or by just intending to perform a movement or imagining the performing of a movement, the user may control the execution and operation of the program to perform almost any general computerized task.

It is noted that after implantation of the stimulating electrode set(s) or the optical stimulating generator (of FIG. 14 hereinbelow) in or near the visual cortex of the user, the user may be subjected to a testing period for "mapping" the perceived virtual images produced by the stimulation (electrical or photic) of various different locations of the visual cortex. For example, the visual cortex is stimulated at one specific visual cortical location and the user is requested to manually point out the location of the perceived virtual image resulting from the local stimulation by moving his hand (or by intending to move his hand or imagining to move his hand to point to the location in the FOV at which the virtual image is performed. The parameters of the movement are computed by processing the signals resulting from the movement or the intended or imagined movement as recorded at the motor and/or pre-motor regions of the cortex. In this way, by repeating the stimulation and changing the location of stimulation on the visual cortex (for example, by changing the location of the stimulating electrodes used for stimulation on an ECOG electrode array or other electrode array), the positions of the virtual images in the user's FOV may be mapped.

Moreover, since the stimulations may be repeated a large number of times for each individual stimulation location and the resulting data may be processed and statistically analyzed to study the accuracy and repeatability of the prediction of the end target of the user's movement or intended movement or imagined movement. This statistical database may be useful in estimating the size and/or shape and/or any other parameters of the virtual GUI or any of its virtual components in order to optimize the reliability of the interaction of the user with the virtual GUI. Such testing/mapping periods may be useful by allowing to individually design visual cortex stimulation patterns and virtual GUI shapes and forms for each individual user and to ensure a high degree of reliability of the individual user interactions with the virtual GUI.

Moreover, receiving the user's verbal responses describing the virtual image perceived by the user as a result of various different forms of stimulation at different locations on the visual vortex may be used to generate a "library" of stimulation parameters useful in producing different shapes and sizes (and possibly colors) of images that may be used to present the different types of virtual GUIs to the user and may also be useful in presenting more complicated forms of virtual images to the user such as, for example alphanumeric characters and various different graphical symbols.

It will be appreciated that while the system 50 discloses the use of ECOG electrode arrays for stimulating the visual cortical regions and for recording signals from motor and/or pre-motor signals this is not obligatory to practicing the invention and other different types of electrodes (or electrode arrays may be used in embodiments of the systems disclosed herein. For example, UTAH electrode arrays with microelectrodes that may penetrate the surface of the cortex may be used in some embodiments. In other embodiments of the systems of the present application, either the sensing/recording or the stimulation or both may be performed using other methods or devices of cortical sensing and/or stimulation.

In accordance with some embodiments, the systems may use, injectable electronic electrode arrays such as disclosed by the articles by Chong Xie, et al. (*Nature Materials*, Vol. 14, December 2015, Pp. 1286-1292), or by Guosong Hong, et al. (*Nano Letters*, Vol. 15, August 2015, Pp. 6979-6984). Or by Jia Liu et al. (*Nature Nanotechnology*, Vol. 10, July 2015, Pp. 629-636.) referenced hereinabove.

In accordance with other embodiments, the system may use stentrodes as disclosed by Thomas J. Oxley et al. (*Nature Biotechnology*, Vol. 34, No. 3, February 2016).

In accordance with some other embodiments, the systems may use the flexible, foldable, actively multiplexed, high-density electrode Arrays disclosed by Jonathan Viventi, et al (*Nature Neuroscience*, Vol. 14, No. 12, Pp. 1599-1605).

Reference is now made to FIGS. 7-12 which are schematic diagrams illustrating several different types of virtual GUIs usable in some embodiment of the systems of the present application.

Figure 7:
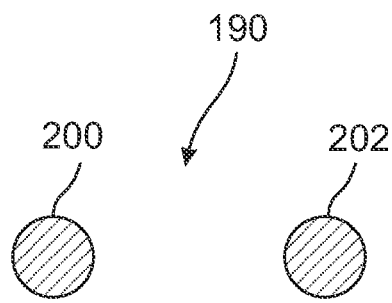
FIGS. 7, 8, 9, 10, 11 and 12 are schematic diagrams illustrating several different types of virtual GUIs usable in some embodiment of the systems of the present application.

Turning to FIG. 7, the GUI 190 includes two virtual images of circles 200 and 202. The circles 200 and 202 may be hollow or filled and may represent a binary decision. The left circle may represent a positive decision and the right circle may represent a negative decision. For example if the program presenting the GUI needs instructions (for example, to activate one of the auxiliary sensors 18 of FIG. 1), the system presents the virtual GUI 190 to the user, by stimulating the visual cortex of the user. If the user wants to activate the sensor, the user may move one of his/her hands or intend to move the or imagine moving the hand towards the place that he or she perceives the left circle 200 to be within his/her field of view. The program operating the system may then process the signals recorded in the motor and/or pre-motor cortex of the user and decodes the amplitude and direction of the movement or of the intended/imagined movement. If the movement's target falls within the area of the left circle 200, the program may interpret this as a "yes" instruction and may activate the sensor and may also (if necessary proceed to present to the user another choice by presenting another suitable virtual GUI. If the movement's target falls within the area of the right circle 202, the program may interpret this as a "no" instruction, does not activate the sensor and may (if necessary) proceed to present another virtual GUI to.

Figure 8:
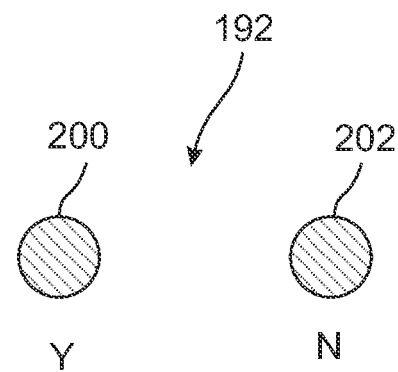

Turning to FIG. 8, the virtual GUI 192 is similar to the GUI 190, except that it also includes images of the characters "Y" and "N" presented below the circles 200 and 202, respectively to assist the user to recognize the functional aspects of the virtual GUI 190.

In some embodiments, the virtual GUI may be similar to a typical dialogue box (such as, for example the dialogue boxes presented on a computer display for interacting with a program operating on the computer. For example, such a virtual dialog box may a virtual image of a rectangular shape including therein two or more virtual images of buttons and alphanumeric characters or text indicating the various selections the user may choose.

The virtual GUIs contemplated herein may also include virtual GUIs usable for enabling the user to input to the program quantitative instructions. For example, the virtual GUIs may include virtual images of "analog" or "quasi-analog" slider type controls that may allow the user to select a value of one or more parameters in a more quantitative manner.

Figure 9:
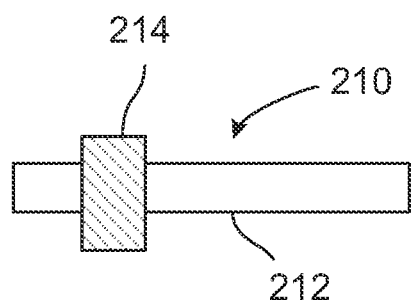

Turning to FIG. 9, the virtual GUI 210 is a virtual image of a slider type control comprising a virtual image of a horizontal bar 212 and a virtual image of a second rectangle 214 virtually movable along the horizontal bar 212. In operation, when the user moves his hand or imagines moving his hand in a certain direction along the horizontal bar 212, the signals sensed in the motor and/or pre-motor cortex of the user may be processed and decoded to compute the actual or intended or imagined movement's parameters (such as, for example, direction, amplitude and endpoint within the FOV). These parameters may be used to compute the position intended by the user to move the second rectangle 214 into on the horizontal bar 212. The program may (in some embodiments) stimulate the visual cortex to "move" the rectangle 214 on the horizontal bar 212 to a new (intended) position (in order to provide visual feedback to the user) and may use the position data to increase or decrease a value of a control parameter. For example, using the virtual GUI 210, the user may control the gain of a sound amplifier (for volume control), change the sensitivity of a sensor, and perform similar tasks in a general computing environment.

Figure 10:
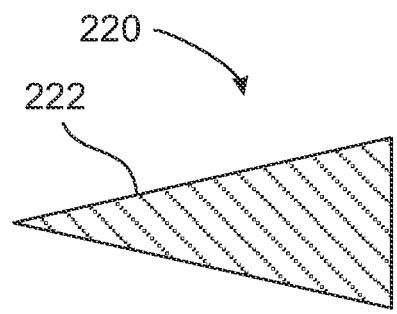

Turning now to FIG. 10, the virtual GUI 220 represents (schematically) another usable type of virtual slider GUI including virtual image of a wedge 222. The user may use the virtual GUI 220 by moving and/or intending to move and/or imagining the movement of his/her hand in a horizontal direction to a desired location on the wedge 222. The processing and decoding of the signals sensed in the motor and/or pre-motor cortex may be performed as disclosed hereinabove with respect to FIG. 9.

Figure 11:
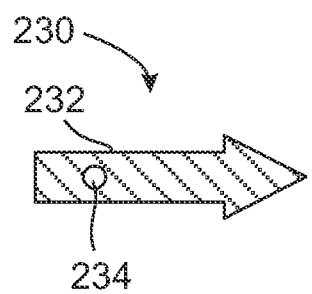

Turning to FIG. 11, the virtual GUI 230 includes the virtual image of an arrow-like shape 232 and a dot-like shape 234. The user may interact with the virtual GUI 230 by moving his/her hand (and/or by intending and/or imagining the moving of the hand) in a movement intended to rotate the arrow-like shape 232 around the dot-like shape 234 to input to the program an intended direction within the FOV of the user. The processing and decoding of the signals sensed in the motor and/or pre-motor cortex may be performed as disclosed hereinabove with respect to FIG. 9.

Figure 12:
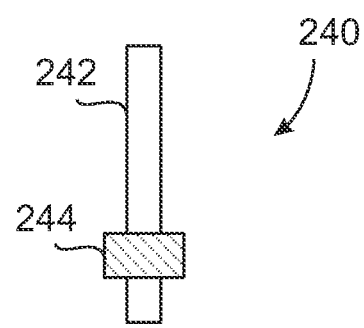

Turning to FIG. 12, the virtual GUI 240 is a virtual image of a slider type control comprising a virtual image of a vertical bar 242 and a virtual image of a second rectangle 244 virtually movable along the horizontal bar 242. The virtual GUI 240 is presented and operated as described in detail for the virtual GUI 210 of FIG. 9, except that the virtual image of the vertical bar 242 is oriented vertically and the virtual image of the rectangle 244 is virtually slidable vertically.

Figure 13:
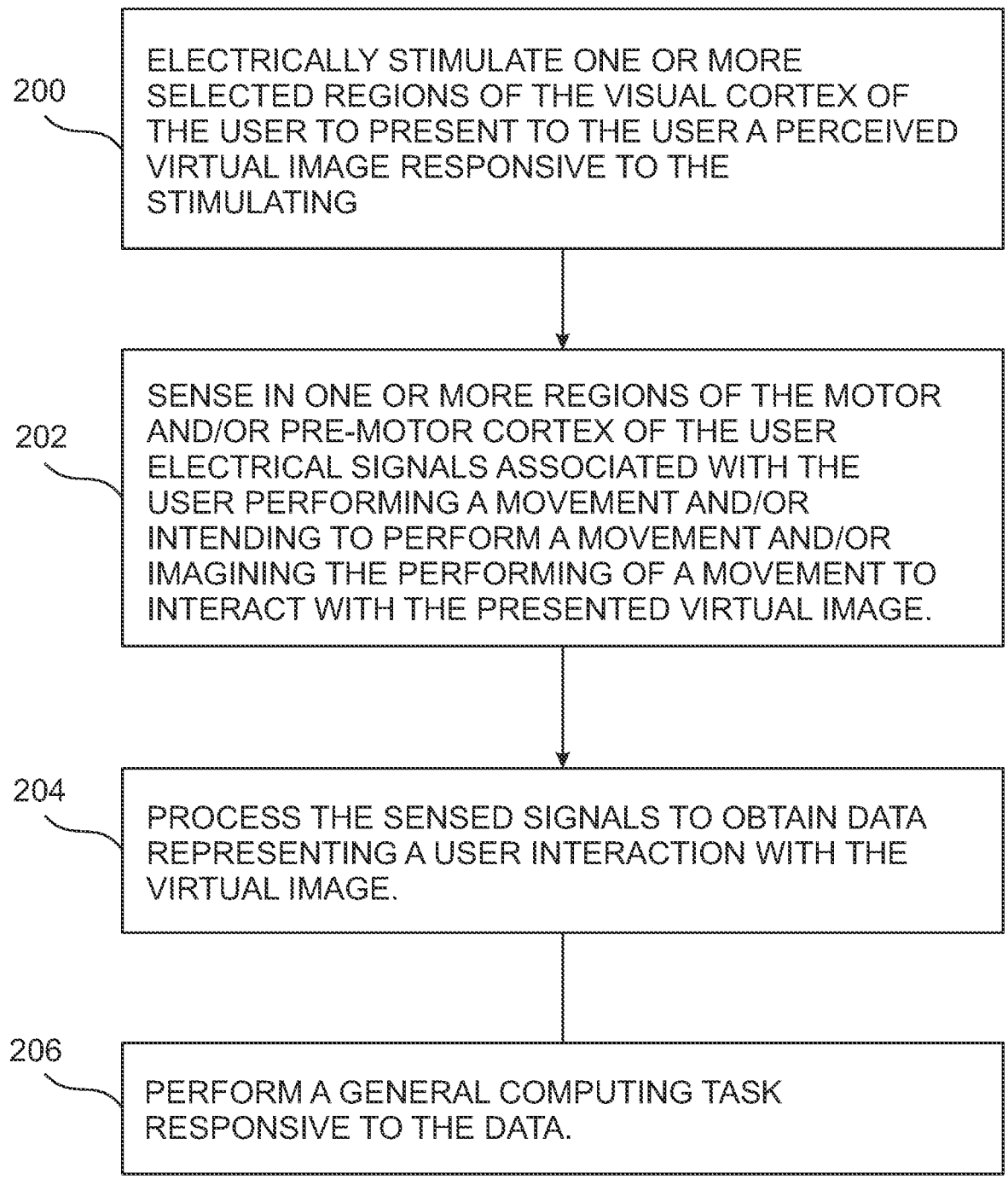
FIG. 13 is a schematic flow chart diagram illustrating the steps of a method of using a system for presenting a virtual GUI, in accordance with an embodiment of the methods of the present application.

Reference is now made to FIG. 13 which is a schematic flow chart diagram illustrating the steps of a method of using a system for presenting a virtual GUI, in accordance with an embodiment of the methods of the present application.

The method that may be performed by any of the systems (for example, by a software program operative on one or more of the processor/controller(s) of the systems disclosed hereinabove, may operate by electrically stimulating one or more selected regions of the visual cortex of a user a perceived virtual image to present to the user a perceived virtual image responsive to the stimulating (step 200). The regions of the visual cortex that may be stimulated in step 200 may include but are not limited to, the primary visual cortex (V1), striate cortex, the supplementary visual cortex, the secondary visual cortex (V2), the pre-striate cortex, the cortical visual area 4 (V4), the medial temporal (MT) lobe of the visual cortex (V5), the dorso-medial (DM) visual area (V6), BA17, BA 18 and BA19 and any combinations of these areas.

The system senses electrical signals from one or more regions of the motor and/or pre-motor cortex of the user. The sensed signals are associated with the user performing a movement and/or intending to perform a movement and/or imagining the performing of a movement to interact with the presented virtual image (step 202). The regions of the cortex that the sensing of step 202 may be performed in may include but are not limited to, the primary motor cortex, the pre-motor cortex, BA4, the pre-central gyrus, the supplementary motor cortex (SMC), BA6, and any combinations thereof.

The system processes the sensed signals to obtain data representing a user interaction with the virtual image (step 204) and performs a general computing task responsive to the data (step 204). In some embodiments of the method, the data obtained by processing the sensed signals may include one or more parameters of the movement performed by the user or of a movement intended to be performed by the user or imagined by the user. For example, the data may be indicative of the direction and amplitude of the actual movement or the imagined movement. The system may use this data to compute if the end target position of the movement falls within a predetermined area of the virtual GUI as disclosed hereinabove. For example with respect to the virtual GUI disclosed in FIG. 8, if the system detects that the end target of the movement (or imagined movement) falls within the virtual image circle 200 of the virtual GUI 192, the program of the method interprets this as a user selection of an answer "Yes" and proceeds to respond to this selection by performing the selected software implemented action. The action may be any suitable action of a general computing task as is known in the art. For example, the action may be changing a value of a variable in memory (such as, but not limited to, a software "Flag") reading the next instruction of a machine code, presenting another virtual GUI to the user, or any other suitable software implemented action or step.

In another example, with respect to the virtual GUI 220 of FIG. 10, the system may compute from the direction and amplitude of the movement (or imagined movement) the position of the intended target of the movement on the wedge-like image 22 and may compute from this position a digitized value for the intended scale position. For example, if the wedge-like virtual image 222 is used to adjust the amplitude of the signal provided to a loudspeaker (not shown), the determined position along the wedge-like virtual image 22 which the user indicated by the movement (real and/or imagined) may be used to change the amplitude of a voltage waveform supplied to the loudspeaker by the program.

The methods and systems disclosed herein may allow the user to interact with and to control the operation of any suitable software program in any general computing environment within or external the system and perform any computer task, without the need to display to the user a GUI by presenting the GUI on a display device (such as a physical computer screen, VR goggles, augmented reality goggles HUD, or any other type of physical display device or projection device observable by the user through the user's eyes. This is achieved by direct stimulation of the visual cortex as disclosed hereinabove and using signals sensed in the motor and/or pre-motor cortical region(s) to interact with the virtual GUI perceived by the user.

It is noted that while the systems for providing artificial vision to blind people disclosed in the Dobelle and Dobelle et al. publications referenced hereinabove has limited resolution mainly due to the limited number of electrodes available in the ECOG electrode arrays at the time of implementation the systems. However, the virtual GUI systems of the present application contemplate the use of currently available electrode arrays which may include several hundred to several thousands of individual electrodes.

The use of such high density, high resolution electrode arrays, UTAH arrays, or high density injectable mesh type electronics disclosed in the references by Chong Xie, et al. (*Nature Materials*, Vol. 14, December 2015, Pp. 1286-1292), or by Guosong Hong, et al. (*Nano Letters*, Vol. 15, August 2015, Pp. 6979-6984), or by Jia Liu et al. (*Nature Nanotechnology*, Vol. 10, July 2015, Pp. 629-636.), referenced hereinabove, or of any other type of high resolution electrode arrays in the systems of the present application may allow a much higher resolution in the local stimulation of cortical micro-regions which may allow the presented visual image to have high resolution enabling the presentation of text and imagery at high resolution. As such, the systems disclosed herein may allow the presentation of text and imagery required for presenting the user with various useful types of information. For example, by using the systems disclosed in the present application, the user may be able to operate a web browser program to retrieve and present to the user virtual images of content available on the internet or on a database.

It will be appreciated that the virtual GUIs that may be used in the systems of the present application are not limited to the specific embodiments illustrated in FIGS. 7-12. Rather, many other different types of virtual GUIs may be used and implemented in accordance with some embodiments of the systems and methods of the present application. Such types may be similar to any type of GUI known in the art and used for interaction of a user with a computer, a smartphone or any other computer-like devices known in the art.

In some embodiments, the systems disclosed in the present application may present several of virtual images of different types within a single virtual GUI presented to the user. For example, a virtual GUI may include one or more "dialogue boxes", one or more decision/selection "buttons", one or more virtual sliders and also virtual text or alphanumeric characters.

It is noted that while all the embodiments of the systems disclosed hereinabove rely on stimulation of the visual cortex by applying electrical stimuli through electrodes to the visual cortex and use electrodes for sensing electrical signals at the motor and/or pre-motor cortex, this is by no means obligatory to practicing the invention. Rather other methods for sensing and stimulating may be used in the systems of the present application.

Figure 14:
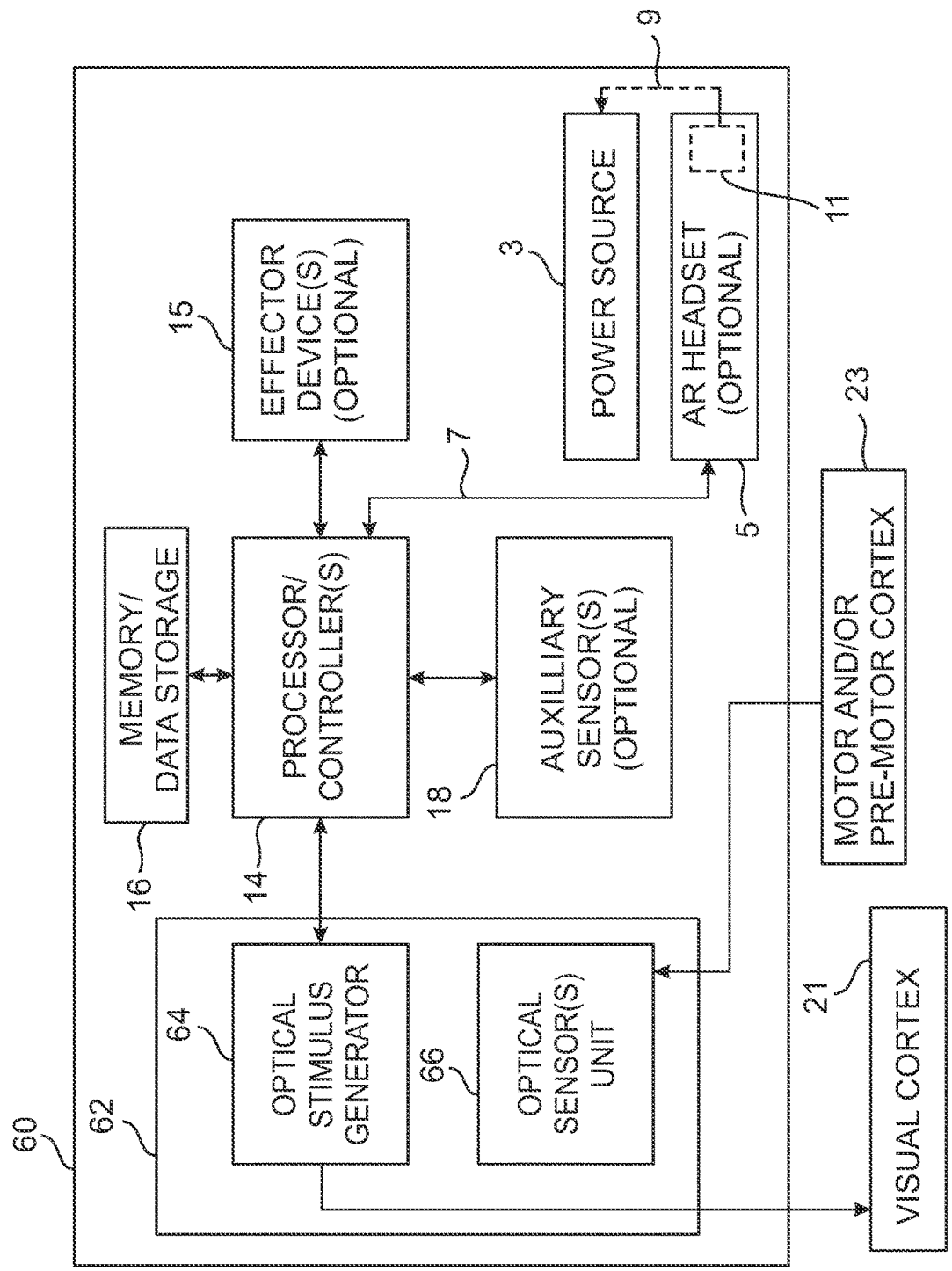
FIG. 14 is a schematic block diagram illustrating a general virtual GUI system having an optical stimulation and sensing unit for optically stimulating an optogenetically modified visual cortex of a user and for sensing/recording optical signals from an optogenetically modified motor and/or premotor cortex of the user, in accordance with some embodiments of the systems of the present application.

Reference is now made to FIG. 14 which is a schematic block diagram illustrating a general virtual GUI system having an optical stimulation and sensing unit for optically stimulating an optogenetically modified visual cortex of a user and for sensing/recording optical signals from an optogenetically modified motor and/or pre-motor cortex of the user, in accordance with some embodiments of the systems of the present application.

The system 60 may include the processor/controller(s) 14, the effector device(s) 15, the auxiliary sensors 18, the memory/data storage 16, the power source 3 and the AR headset 5 that may be connected and operative as disclosed hereinabove in detail with respect to the system 10 of FIG. 1 hereinabove. However, instead of the sensing/stimulating electrode set(s) of the system 10, the system 60 includes an optical stimulation and recording unit 62 in suitable communication with the processor/controller(s) 14.

The optical stimulation and recording unit 62 may include an optical stimulus generator 64 for delivering optical stimulating signals to the visual cortex and an optical sensor(s) unit 66 for sensing optical signals associated with neuronal activity in the motor and/or pre-motor cortex. The optical stimulus generator 64 may be any suitable type of light source, such as for example a laser, a LED laser, a laser diode array a quantum dot array or any other suitable biocompatible light source that may be implanted near the surface of the visual cortex.

The optical sensor(s) unit 66 may be implemented as any optical device having a plurality of light sensing elements, such as, for example, a photodiode array, a phototransistor array, a multi-pixel CMOS imaging array, a CCD array imager, or any other type of biocompatible implantable imaging device suitable for sensing optical signals associated with neuronal activity in the motor and/or pre-motor cortex.

The optical stimulation and recording unit 62 may include all the necessary electronic circuitry for receiving controlling instructions from the processor/controller(s) 14 and for activating the optical stimulus generator to optically stimulate the visual cortex with appropriate light pulses.

The optical stimulation and recording unit 62 may also include all the necessary electronic circuitry for receiving voltage or current signals representing light sensed by the optical sensor unit(s) 66 at the motor and/or pre-motor cortex and for processing and/or conditioning the received voltage or current signals and for sending the processed signals to the processor/controller(s) 14 and for further processing and decoding. Such circuitry (not shown in detail in FIG. 14 for the sake of clarity of illustration) may include, inter alia filtering circuitry, digital to analog converters, analog to digital converters, electronic clock circuits, multiplexing circuits and any other necessary electronics.

The neurons in the visual cortex and in the motor/pre-motor cortex of the user may be optogenetically treated to express suitable molecules for emitting light when the neurons are depolarized (for motor/pre-motor cortex neurons) and for responding to light stimulation by depolarization (for visual cortex neurons). Such optogenetic molecules may include, among others, naturally occurring channel rhodopsins (for enabling light induced depolarization of the neurons expressing them), luminescent calcium indicators, and genetically encoded voltage sensors (for emitting light when the neurons are depolarized). The methods for inducing expression of such optogenetic molecular tools using viral vectors or other methods, are well known in the art, are not the subject matter of the present application and are therefore not disclosed in detail in the present application. Briefly, such methods may be found in the optogenetic literature and in the following references cited hereinabove: Boyden et al. (*Nature Neuroscience*, Vol. 8, No. 9, September 2005, Pp. 1263-1268). Karl Deisseroth. (Optogenetics", *Nature Methods*, Vol. 8, No. 1, January 2011, Pp. 26-29). Karl Deisseroth. (*Nature Neuroscience*, Vol. 18, No. 9, September 2015, Pp. 1213-1225). Berndt et at. (*Science*, Vol. 349, No. 6248, Aug. 7, 2015, Pp. 590-591) and in Emiliani et al. (Journal of Neuroscience, Oct. 14, 2015-35(41):13917-13926).

It will be appreciated by those skilled in the art that it may be possible as is contemplated herein to mix and match optical and electrical components as desired in the systems of the present application. For example, in some embodiments of the systems, the stimulation of the visual cortex may be performed by optical means (such as, for example, the optical stimulus generator 64 of FIG. 14), and the sensing in the motor and/or pre-motor cortex may be performed by the sensing electrode set(s) 12B of FIG. 2 or by the ECOG electrode array 142 of FIG. 4). In such embodiments it is not necessary to optogenetically treat the motor and/or pre-motor cortical regions since the sensing is not optical.

In some other embodiments of the systems, the stimulation of the visual cortex may be performed by electrode means (such as, for example, by the stimulating electrode set(s) 12A of FIG. 2 or the ECOG electrode array 144 of FIG. 4), and the sensing of motor and/or pre-motor signals may be performed by optical sensing means (such as, for example, the optical sensor units 66 of FIG. 14). In such embodiments it is not necessary to optogenetically treat the visual cortical regions since the stimulation is not optical.

It will be appreciated that the practicing of the present invention is not limited to the use of intracranially implanted electrode sets such as the ECOG electrode arrays described in the exemplary implementation disclosed hereinabove and illustrated in the figures. Different types of electrodes, electrode sets may also be used for stimulating and for sensing signals in the above described cortical regions. For example, intracalvarial electrode systems, such as, for example the intracalvarial electrodes and implants disclosed in international patent application publication No. WO/2016/049789, published on 7 Apr. 2016, incorporated herein by reference in its entirety, may also be used in the systems of present application with the advantage that such intracalvarial electrodes may be placed within the calvarial bone without the need for complicated highly invasive surgery. Thus, the present invention contemplates and includes the use of intracalvarial electrodes and/or electrode sets disposed within the calvarial bone of the skull of the user to stimulate the above described cortical regions functionally associated with visual functioning and/or to sense electrical signals in the cortical regions associated with motor function.

The systems and methods of the present application may thus be used to enable a user to perform many types of general computer tasks and may be usable as enabling interaction of a user with many types of software programs operating in a computing environment.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A virtual user interface system comprising:
one or more stimulating electrode sets including a first plurality of electrodes for electrically stimulating one or more regions of the visual cortex of the user to present to the user a perceived virtual image responsive to the stimulating;
one or more sensing electrode sets including a second plurality of electrodes for sensing electrical signals in one or more regions of the motor and/or pre-motor cortex of the user;
at least one processor/controller suitably electrically coupled to the one or more stimulating electrode sets and to the one or more sensing electrode sets, the processor/controller is programmed for electrically stimulating one or more selected regions of the visual cortex of the user to present to the user a perceived virtual image responsive to the stimulating, sensing electrical signals from the one or more regions of the motor and/or pre-motor cortex of the user, the sensed signals resulting from the user performing a movement and/or intending to perform a movement and/or imagining the performing of a movement to interact with the presented virtual image, processing the sensed signals to obtain computed data indicative a user interaction with the presented virtual image, and performing a general computing task responsive to the computed data; and
a power source for providing power to the system.

2. The system according to claim 1, wherein the one or more stimulating electrode sets and/or the one or more sensing electrode sets are selected from, an electrode array, an Ecog electrode array, a UTAH electrode array, an injectable electrode array, a mesh implantable electrode array, a flexible electrode array, a foldable electrode array, neural dust, a stentrode array and any combinations thereof.

3. The system according to claim 1, wherein the perceived image is an image selected from, an image comprising one or more geometrical shapes, an image comprising alphanumerical text, an image comprising one or more colored regions, an image comprising one or more lines, and any non-mutually exclusive combinations thereof.

4. The system according to claim 1, wherein the general computing task is a computing task requiring input from the user for the operation thereof.

5. The system according to claim 1, wherein the at least one processor/controller is programmed to perform the processing of the electrical signals sensed in one or more regions of the motor and/or pre-motor cortex of the user by computing one or more parameters of the movement performed by the user and/or imagined by the user and using the one or more parameters to determine if the intended end target of the imagined movement and/or the performed movement falls within or in the vicinity of a perceived virtual image presented to the user by the stimulating.

6. The system according to claim 1, wherein the one or more sensing electrode sets and the one or more stimulating electrode sets are selected from,
   a single electrode array including the one or more stimulating electrode set and the one or more stimulating electrode set, and
   at least one electrode array including the one or more stimulating electrode sets and at least one electrode array including the one or more sensing electrode set(s).

7. The system according to claim 1, wherein the at least one processor/controller is programmed to control, based on the user's interactions with the virtual image, the operation of one or more devices, the one or more devices are selected from devices external to the body of the user, devices implanted in the user's body and devices worn by or attached to the user.

8. The system according to claim 7, wherein the one or more devices are selected from one or more sensors, one or more effectors, an effector device attached to or carried by the user, an effector device carrying the user, a prosthesis, a motorized vehicle, a land vehicle, an airborne vehicle, a marine vehicle, an effector device in the vicinity of the user, a remote effector device, a drone, a motorized exoskeleton device carrying the user, a robotic device operable by the user, a sound source, an ultrasound source, an audio speaker, a visible light source, an IR light source, a device for therapeutically treating the user, a diagnostic device, an augmented reality headset and any non-mutually exclusive combinations thereof.

9. The system according to claim 1, wherein the one or more sensing electrode sets are configured to be disposed on or within or in the vicinity of, the primary motor cortex, the pre-motor cortex, BA4, a precentral gyrus, a supplementary motor cortex (SMC), BA6, and any combinations thereof.

10. The system according to claim 1, wherein the one or more stimulating electrode sets are configured to be disposed on or within or in the vicinity of, the primary visual cortex (V1), striate cortex, supplementary visual cortex, secondary visual cortex (V2), prestriate cortex, cortical visual area 4 (V4), medial temporal (MT) lobe of the visual cortex (V5), dorsomedial (DM) visual area (V6), BA17, BA 18 and BA19 and any combinations thereof.

11. The system according to claim 1, wherein the at least one processor/controller is selected from, a microprocessor, a microcontroller, a CPU, a GPU, a DSP, a cluster of processors, a parallel computing network, a quantum computing device, a quantum computer, and any combinations thereof.

12. The system according to claim 1, wherein the one or more sensing electrode sets and the one or more stimulating electrode sets are intracalvarial electrodes implanted within the calvarial bone of a skull of the user.

13. The system according to claim 12, wherein the one or more sensing electrode sets and/or the one or more stimulating electrode sets are intracalvarial electrodes implanted within the calvarial bone of a skull of the user overlying one or more regions of the cortex of the user.

14. The system according to claim 1, wherein the at least one processor/controller is in wireless communication with an external processing/programming unit(s) for telemetrically communicating data from the at least one processor controller to the external processor/programing unit(s).

15. The system according to claim 14, wherein the telemetrically communicating data comprises offloading of some or all of the computational burden to the external processing/programming unit(s) by using cloud computing.

16. The system according to claim 15, wherein the external processing/programming unit(s) is selected from, remote computer(s), server(s), a cluster of computers.

17. A method for using a virtual user interface, the method comprising the steps of:
   electrically stimulating one or more selected regions of the visual cortex of the user to present to the user a perceived virtual image responsive to the stimulating;
   sensing electrical signals from one or more regions of the motor and/or pre-motor cortex of the user, the sensed signals are associated with the user performing a movement and/or intending to perform a movement and/or imagining the performing of a movement to interact with the presented virtual image;
   processing the sensed signals to obtain data representing a user interaction with the virtual image; and
   performing a general computing task responsive to the data.

18. The method according to claim 17, wherein the step of performing is selected from, performing a selection, performing a decision, and providing quantitative information.

19. The method according to claim 17, wherein the step of electrically stimulating comprises stimulating one or more of, primary visual cortex (V1), striate cortex, supplementary visual cortex, secondary visual cortex (V2), prestriate cortex, cortical visual area 4 (V4), medial temporal (MT) lobe of a visual cortex (V5), dorsomedial (DM) visual area (V6), BA17, BA 18 and BA19.

20. The method according to claim 17, wherein the step of sensing electrical signals comprises sensing electrical signals in one or more of, the primary motor cortex, the pre-motor cortex, BA4, precentral gyrus, supplementary motor cortex (SMC), BA6, and any combinations thereof.

21. The method according to claim 17, wherein the method also includes the step of controlling the operation of one or more devices responsive to the interaction of the user with the presented virtual image.

22. The method according to any claim 17, wherein the step of processing the sensed signals comprises computing from the sensed signals one or more parameters of a movement performed by the user and/or imagined by the user and using the one or more parameter to determine if the intended end target of the imagined movement and/or the performed movement falls within or in the vicinity of a perceived virtual image presented to the user by the stimulating.

23. The method according to claim 17, wherein the general computing task comprises operating a browser program for presenting one or more virtual images comprising alphanumeric data and/or graphic content and/or, text, and/or video images to the user by directly stimulating of the visual cortex of the user.

24. The method according to claim 17, wherein the general computing task comprises a program for operating one or more devices.

25. The method according to claim 24, wherein the one or more devices are selected from one or more sensors, one or more effectors, an effector device attached to or carried by the user or worn by the user, an effector device carrying the user, a prosthesis, a motorized vehicle, a land vehicle, an airborne vehicle, a marine vehicle, an effector device in the vicinity of the user, a remote effector device, a drone, a motorized exoskeleton device carrying the user, a robotic device operable by the user, a sound source, an ultrasound source, an audio speaker, a visible light source, an IR light source, a device for therapeutically treating the user, a diagnostic device, an augmented reality headset, and any non-mutually exclusive combinations thereof.

26. A virtual user interface system comprising:
  one or more stimulating devices for stimulating neurons in one or more regions of the visual cortex of the user to present to the user a perceived virtual image responsive to the stimulating;
  one or more sensing devices for sensing signals associated with neuronal activity in one or more regions of the motor and/or pre-motor cortex of the user;
  at least one processor/controller suitably coupled to the one or more stimulating devices and to the one or more sensing devices, the processor/controller is programmed for stimulating one or more selected regions of the visual cortex of the user to present to the user a perceived virtual image responsive to the stimulating, sensing signals from the one or more regions of the motor and/or pre-motor cortex of the user, the sensed signals resulting from the user performing a movement and/or intending to perform a movement and/or imagining the performing of a movement to interact with the presented virtual image, processing the sensed signals to obtain computed data indicative a user interaction with the presented virtual image, and performing a general computing task responsive to the computed data; and
  a power source for providing power to the system.

27. The system according to claim 26, wherein the one or more stimulating devices are selected from one or more stimulating electrode set(s) and one or more light emitting devices.

28. The system according to claim 27, wherein the one or more light emitting devices are selected from one or more lasers, one or more light emitting diodes, one or more diode lasers, one or more quantum dots, one or more light emitting diode arrays, one or more laser diode arrays, one and more quantum dot arrays, and any combinations thereof.

29. The system according to claim 26, wherein the one or more sensing devices are selected from one or more sensing electrode set(s) and one or more light sensitive devices.

30. The system according to claim 29 wherein the one or more light sensitive devices are selected from, one or more photosensors, one or more photosensor arrays, one or more photodiodes, one or more photodiode arrays, one or more phototransistors, one or more phototransistor arrays, a multi-pixel CMOS imaging array, a CCD array imager and any non mutually exclusive combinations thereof.

31. A method for using a virtual user interface, the method comprising the steps of:
  stimulating one or more selected regions of the visual cortex of the user to present to the user a perceived virtual image responsive to the stimulating;
  sensing signals from one or more regions of the motor and/or pre-motor cortex of the user, the sensed signals are associated with the user performing a movement and/or intending to perform a movement and/or imagining the performing of a movement to interact with the presented virtual image;
  processing the sensed signals to obtain data representing a user interaction with the virtual image; and
  performing a general computing task responsive to the data.

32. The method according to claim 31, wherein the step of sensing is selected from the steps of,
  sensing electrical signals from one or more regions of the motor and/or pre-motor cortex of the user, and
  sensing optical signals from one or more regions of the motor and/or pre-motor cortex of the user.

33. The method according to claim 31, wherein the step of stimulating is selected from the steps of,
  Optically stimulating one or more selected regions of the visual cortex of the user to present to the user a perceived virtual image responsive to the stimulating, And,
  electrically stimulating one or more selected regions of the visual cortex of the user to present to the user a perceived virtual image responsive to the stimulating.

* * * * *